United States Patent
Ding et al.

(10) Patent No.: US 10,391,222 B2
(45) Date of Patent: Aug. 27, 2019

(54) DEVICES FOR UREA ELECTROLYSIS AND METHODS OF USING SAME

(71) Applicants: Baxter International Inc., Deerfield, IL (US); Baxter Healthcare SA, Glattpark (Opfikon) (CH)

(72) Inventors: Yuanpang Samuel Ding, Long Grove, IL (US); Cristian Adolfo Menzel Bueno, Braine-l'Alleud (BE); Rosa Yeh, Libertyville, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 496 days.

(21) Appl. No.: 15/074,388

(22) Filed: Mar. 18, 2016

(65) Prior Publication Data
US 2017/0189594 A1  Jul. 6, 2017

Related U.S. Application Data

(60) Provisional application No. 62/273,863, filed on Dec. 31, 2015.

(51) Int. Cl.
*A61M 1/16* (2006.01)
*B01D 61/42* (2006.01)
(Continued)

(52) U.S. Cl.
CPC .......... *A61M 1/169* (2013.01); *A61M 1/1672* (2014.02); *A61M 1/1696* (2013.01);
(Continued)

(58) Field of Classification Search
CPC ....... A61M 1/1696; C02F 1/469; C02F 1/467; C02F 1/4672; C02F 1/4674; C25B 3/02
See application file for complete search history.

(56) References Cited

U.S. PATENT DOCUMENTS 3,472,766 A   10/1969  Shlomo
4,388,163 A *  6/1983  Richter ............... A61M 1/3486
                                              204/252

(Continued)

FOREIGN PATENT DOCUMENTS

EP   1857439    11/2007
EP   2446908     5/2012
(Continued)

OTHER PUBLICATIONS

Lehmann, H. D., R. Marten, and C. A. Gullberg. "How to catch urea? Considerations on urea removal from hemofiltrate." Artificial Organs 5, No. 3 (1981): 278-285.
(Continued)

*Primary Examiner* — Salil Jain
(74) *Attorney, Agent, or Firm* — K&L Gates LLP

(57) ABSTRACT

The present disclosure provides devices and methods of using same for cleansing a solution (e.g., a salt solution) of urea via electrooxidation, and more specifically to cleansing a renal therapy solution/dialysis solution of urea via electrooxidation so that the renal therapy solution/dialysis solution can be used or reused for treatment of a patient. In an embodiment, a device for the removal of urea from a fluid having urea to produce a cleansed fluid includes a urea decomposition unit and an electrodialysis unit.

43 Claims, 14 Drawing Sheets

(51) Int. Cl.
*B01D 61/46* (2006.01)
*C25B 3/02* (2006.01)
*C25B 9/06* (2006.01)
*C02F 1/469* (2006.01)

(52) U.S. Cl.
CPC .......... *B01D 61/42* (2013.01); *B01D 61/422* (2013.01); *B01D 61/46* (2013.01); *C02F 1/469* (2013.01); *C25B 3/02* (2013.01); *C25B 9/06* (2013.01)

(56) References Cited

U.S. PATENT DOCUMENTS

| | | | |
|---|---|---|---|
| 4,391,680 A * | 7/1983 | Mani | B01D 61/445 204/296 |
| 4,473,449 A * | 9/1984 | Michaels | A61M 1/1696 205/555 |
| 5,944,684 A | 8/1999 | Roberts et al. | |
| 6,429,294 B1 * | 8/2002 | Masuda | A61M 1/1696 436/74 |
| 6,506,305 B2 | 1/2003 | Morita et al. | |
| 7,867,214 B2 | 1/2011 | Childers et al. | |
| 8,715,221 B2 | 5/2014 | Curtin et al. | |
| 8,876,753 B2 | 11/2014 | Roberts et al. | |
| 2003/0165743 A1 * | 9/2003 | Horikiri | G02F 1/1525 429/300 |
| 2011/0048949 A1 | 3/2011 | Ding et al. | |
| 2012/0156582 A1 * | 6/2012 | Tao | B82Y 30/00 429/454 |
| 2014/0336568 A1 | 11/2014 | Wong | |

FOREIGN PATENT DOCUMENTS

| | | |
|---|---|---|
| EP | 2862584 | 4/2015 |
| GB | 2 403 166 | 12/2004 |
| WO | 2012060700 | 5/2012 |
| WO | 2015124716 | 8/2015 |

OTHER PUBLICATIONS

Ozaki, Hiroaki, and Huafang Li. "Rejection of organic compounds by ultra-low pressure reverse osmosis membrane." Water Research 36, No. 1 (2002): 123-130.

Huang, Chuanhui, and Tongwen Xu. "Electrodialysis with bipolar membranes for sustainable development." Environmental Sscience & Technology 40, No. 17 (2006): 5233-5243.

Xu, Jun, Zhi Wang, Jixiao Wang, and Shichang Wang. "Positively charged aromatic polyamide reverse osmosis membrane with high anti-fouling property prepared by polyethylenimine grafting." Desalination 365 (2015): 398-406.

Cui, Yue, Zhi-Kan Yao, Ke Zheng, Shi-Yuan Du, Bao-Ku Zhu, Li-Ping Zhu, and Chun-Hui Du. "Positively-charged nanofiltration membrane formed by quaternization and cross-linking of blend PVC/P (DMA-co-MMA) precursors." Journal of Membrane Science 492 (2015): 187-196.

Wang, Xiao-lei, Jun-fu Wei, Zhao Dai, Kong-yin Zhao, and Huan Zhang. "Preparation and characterization of negatively charged hollow fiber nanofiltration membrane by plasma-induced graft polymerization." Desalination 286 (2012): 138-144.

International Search Report and Written Opinion issued in related International Patent Application No. PCT/US2016/068698 dated Mar. 30, 2017.

International Search Report and Written Opinion issued in related International Patent Application No. PCT/US2016/068695 dated Mar. 31, 2017.

* cited by examiner

DEVICES FOR UREA ELECTROLYSIS AND METHODS OF USING SAME

PRIORITY CLAIM

The present application claims priority to U.S. Provisional Application No. 62/273,863, filed Dec. 31, 2015, entitled, "Devices for Urea Electrolysis and Methods of Using Same.

CROSS-REFERENCE TO RELATED APPLICATION

The present application shares much of the same written description and drawings with commonly owned and concurrently filed U.S. patent application Ser. No. 15/074,457, entitled "Devices for Urea Electrolysis with Combination Electrodialysis and Urea Oxidation Cell and Methods of Using Same", which also claims priority to U.S. Provisional Application No. 62/273,863.

BACKGROUND

Due to disease or insult or other causes, the renal system can fail. In renal failure of any cause, there are several physiological derangements. The balance of water, ions (e.g., $Na^+$, $K^+$, $Cl^-$, $Ca^{2+}$, $PO_4^{3-}$, $Mg^{2+}$, $SO_4^{2-}$) and the excretion of daily metabolic load of fixed hydrogen ions is no longer possible in renal failure. Further, during renal failure, toxic end products of nitrogen metabolism including, for example, urea, creatinine, uric acid, and others can accumulate in blood and tissues.

Several types of dialysis have been devised (e.g., peritoneal dialysis, hemodialysis, hemofiltration, and hemodiafiltration) for the removal of toxic end products of nitrogen metabolism from blood. These types of dialysis rely on diffusion of urea across a membrane and/or enzymatic degradation of urea. However, degradation of urea is problematic in that it produces toxic end products such as ammonium that must be removed and or trapped to ensure that they are not returned to a patient. Often sorbents are employed during dialysis to bind such toxic end products. These sorbents are expensive and add bulk to a dialysis system making them less suitable to being used in portable or wearable applications. Therefore, there is a need for dialysis systems that can remove urea from blood without generating toxic end products.

SUMMARY

The present disclosure provides devices and methods of using same for cleansing a solution (e.g., a salt solution) comprising urea via electrooxidation. In a first general embodiment, which may be used in combination with any other embodiment described herein unless specified otherwise, a device for the removal of urea from a fluid having urea to produce a cleansed fluid, the device comprises a urea decomposition unit comprising an inlet for entry of the fluid having urea and an outlet for removal of the cleansed fluid, and one or more sets of electrodes having an anode and a cathode with an electrocatalytic surface for decomposition of urea via electrooxidation; and an electrodialysis unit comprising a set of electrodes having an anode and a cathode for separation of a salt solution via electrodialysis, where the salt solution is separated into an acid stream and a basic stream, wherein at least one of (i) the basic stream of the electrodialysis unit is placed in fluid communication with the inlet of the urea decomposition unit, (ii) the acid stream from the electrodialysis unit is placed in fluid communication with the outlet of the urea decomposition unit or (iii) the acid stream is circulated through the electrodialysis unit.

In a second general embodiment, which may be used in combination with any other embodiment described herein unless specified otherwise, the electrodialysis unit comprises a first cell comprising a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming (i) a first compartment between the first bipolar membrane and the first ion exchange membrane and (ii) a second compartment between the first bipolar membrane and the second ion exchange membrane.

In a third general embodiment, which may be used with the second embodiment in combination with any other embodiment described herein unless specified otherwise, the first ion exchange membrane is an anion exchange membrane or a cation exchange membrane.

In a fourth general embodiment, which may be used with the second embodiment in combination with any other embodiment described herein unless specified otherwise, the second ion exchange membrane is an anion exchange membrane or a cation exchange membrane.

In a fifth general embodiment, which may be used with the second embodiment in combination with any other embodiment described herein unless specified otherwise, the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

In a sixth general embodiment, which may be used with the fifth embodiment in combination with any other embodiment described herein unless specified otherwise, the first, second, and third ion exchange membranes are cation exchange membranes, or the first, second, and third ion exchange membranes are anion exchange membranes.

In a seventh general embodiment, which may be used in combination with any other embodiment described herein unless specified otherwise, the electrodialysis unit comprises a cell including a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In an eighth general embodiment, which may be used with the seventh embodiment in combination with any other embodiment described herein unless specified otherwise, the first ion exchange membrane is a cation exchange membrane and the second ion exchange membrane is an anion exchange membrane.

In a ninth general embodiment, which may be used in combination with any other embodiment described herein unless specified otherwise, a power source in the urea decomposition unit provides the electrodes with an electrical charge to activate the electrocatalytic surface of the electrodes.

In a tenth general embodiment, which may be used in combination with any other embodiment described herein unless specified otherwise, a power source in the electrodialysis unit provides the electrodes with an electrical charge to split water in a bipolar membrane into $H^+$ and $OH^-$.

In an eleventh general embodiment, which may be used in combination with any other embodiment described herein unless specified otherwise, the electrodialysis unit separates the salt solution via bipolar membrane electrodialysis.

In a twelfth general embodiment, which may be used in combination with any other embodiment described herein unless specified otherwise, the basic stream of the electrodialysis unit is in fluid communication with the inlet of the urea decomposition unit and the acid stream from the electrodialysis unit is in fluid communication with the outlet of the urea decomposition unit.

In a thirteenth general embodiment, which may be used in combination with any other embodiment described herein unless specified otherwise, the salt solution is a dialysis fluid.

In a fourteenth general embodiment, which may be used with the thirteenth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a fifteenth general embodiment, which may be used in combination with any other embodiment described herein unless specified otherwise, the device includes a tank for the salt solution.

In a sixteenth general embodiment, which may be used in combination with any other embodiment described herein unless specified otherwise, the basic stream includes NaOH.

In a seventeenth general embodiment, which may be used in combination with any other embodiment described herein unless specified otherwise, the acid stream includes HCl.

In an eighteenth general embodiment, which may be used in combination with any other embodiment described herein unless specified otherwise, the anodes in the urea decomposition unit comprise a transition metal and/or mixtures thereof and/or alloys thereof.

In a nineteenth general embodiment, which may be used with the eighteenth embodiment in combination with any other embodiment described herein unless specified otherwise, the transition metal is cobalt, copper, iron, nickel, platinum, palladium, iridium, ruthenium, or rhodium.

In a twentieth general embodiment, which may be used with the eighteenth embodiment in combination with any other embodiment described herein unless specified otherwise, the anodes in the urea decomposition unit comprise nickel, nickel oxide, nickel hydroxide or nickel oxide hydroxide (NiOOH).

In a twenty-first general embodiment, which may be used in combination with any other embodiment described herein unless specified otherwise, the urea decomposition unit includes an alkaline polymeric gel.

In a twenty-second general embodiment, which may be used in combination with any other embodiment described herein unless specified otherwise, the fluid having urea is a dialysis fluid contaminated with urea.

In a twenty-third general embodiment, which may be used in combination with any other embodiment described herein unless specified otherwise, a voltage difference applied across the cathodes and the anodes in the urea decomposition unit is sufficient to produce nitrogen gas, carbon dioxide gas, and water.

In a twenty-fourth general embodiment, which may be used in combination with any other embodiment described herein unless specified otherwise, a renal replacement therapy system includes a dialysis fluid circuit. The dialysis fluid circuit comprises a device for the removal of urea from a dialysis fluid having urea to produce a cleansed dialysis fluid. The device includes a urea decomposition unit comprising an inlet for entry of the dialysis fluid having urea and an outlet for removal of the cleansed dialysis fluid, and a set of electrodes having an anode and a cathode with an electrocatalytic surface for decomposition of urea via electrooxidation; and an electrodialysis unit comprising a set of electrodes having an anode and a cathode for separation of a salt solution via electrodialysis, where the salt solution is separated into an acid stream and a basic stream, wherein at least one of (i) the basic stream of the electrodialysis unit is placed in fluid communication with the inlet of the urea decomposition unit, (ii) the acid stream from the electrodialysis unit is placed in fluid communication with the outlet of the urea decomposition unit, or (iii) the acid stream is circulated through the electrodialysis unit.

In a twenty-fifth general embodiment, which may be used with the twenty-fourth embodiment in combination with any other embodiment described herein unless specified otherwise, the cleansed dialysis fluid recirculates through the dialysis fluid circuit.

In a twenty-sixth general embodiment, which may be used with the twenty-fourth embodiment in combination with any other embodiment described herein unless specified otherwise, the electrodialysis unit comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane.

In a twenty-seventh general embodiment, which may be used with the twenty-sixth embodiment in combination with any other embodiment described herein unless specified otherwise, the first ion exchange membrane is an anion exchange membrane or a cation exchange membrane.

In a twenty-eighth general embodiment, which may be used with the twenty-sixth embodiment in combination with any other embodiment described herein unless specified otherwise, the second ion exchange membrane is an anion exchange membrane or a cation exchange membrane.

In a twenty-ninth general embodiment, which may be used with the twenty-sixth embodiment in combination with any other embodiment described herein unless specified otherwise, the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

In a thirtieth general embodiment, which may be used with the twenty-ninth embodiment in combination with any other embodiment described herein unless specified otherwise, the first, second, and third ion exchange membranes are cation exchange membranes or the first, second, and third ion exchange membranes are anion exchange membranes.

In a thirty-first general embodiment, which may be used with the twenty-fourth embodiment in combination with any other embodiment described herein unless specified otherwise, the electrodialysis unit comprises a cell including a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a thirty-second general embodiment, which may be used with the thirty-first embodiment in combination with any other embodiment described herein unless specified otherwise, the first ion exchange membrane is a cation exchange membrane and the second ion exchange membrane is an anion exchange membrane.

In a thirty-third general embodiment, which may be used with the twenty-fourth embodiment in combination with any other embodiment described herein unless specified otherwise, a power source in the urea decomposition unit provides the electrodes with an electrical charge to activate the electrocatalytic surface of the electrodes.

In a thirty-fourth general embodiment, which may be used with the twenty-fourth embodiment in combination with any other embodiment described herein unless specified otherwise, a power source in the electrodialysis unit provides the electrodes with an electrical charge to split water in a bipolar membrane into $H^+$ and $OH^-$.

In a thirty-fifth general embodiment, which may be used with the twenty-fourth embodiment in combination with any other embodiment described herein unless specified otherwise, the electrodialysis unit separates the salt solution via bipolar membrane electrodialysis.

In a thirty-sixth general embodiment, which may be used with the twenty-fourth embodiment in combination with any other embodiment described herein unless specified otherwise, the salt solution is a dialysis fluid.

In a thirty-seventh general embodiment, which may be used with the thirty-sixth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a thirty-eighth general embodiment, which may be used with the twenty-fourth embodiment in combination with any other embodiment described herein unless specified otherwise, the device includes a tank for the salt solution.

In a thirty-ninth general embodiment, which may be used with the twenty-fourth embodiment in combination with any other embodiment described herein unless specified otherwise, the basic stream includes NaOH.

In a fortieth general embodiment, which may be used with the twenty-fourth embodiment in combination with any other embodiment described herein unless specified otherwise, the acid stream includes HCl.

In a forty-first general embodiment, which may be used with the twenty-fourth embodiment in combination with any other embodiment described herein unless specified otherwise, the anodes in the urea decomposition unit comprise a transition metal and/or mixtures thereof and/or alloys thereof.

In a forty-second general embodiment, which may be used with the forty-first embodiment in combination with any other embodiment described herein unless specified otherwise, the transition metal is cobalt, copper, iron, nickel, platinum, palladium, iridium, ruthenium, or rhodium.

In a forty-third general embodiment, which may be used with the forty-first embodiment in combination with any other embodiment described herein unless specified otherwise, the anodes in the urea decomposition unit comprise nickel, nickel oxide, nickel hydroxide or nickel oxide hydroxide (NiOOH).

In a forty-fourth general embodiment, which may be used with the twenty-fourth embodiment in combination with any other embodiment described herein unless specified otherwise, the urea decomposition unit includes an alkaline polymeric gel.

In a forty-fifth general embodiment, which may be used with the twenty-fourth embodiment in combination with any other embodiment described herein unless specified otherwise, a voltage difference applied across the cathodes and the anodes in the urea decomposition unit is sufficient to produce nitrogen gas, carbon dioxide gas, and water.

In a forty-sixth general embodiment, which may be used with any other embodiment described herein unless specified otherwise, a method of performing a renal replacement therapy includes passing a dialysis fluid having urea through a device. The device includes: a urea decomposition unit comprising an inlet for entry of the used dialysis fluid having urea and an outlet for removal of the cleansed dialysis fluid, and a set of electrodes having an anode and a cathode with an electrocatalytic surface for decomposition of urea via electrooxidation; and an electrodialysis unit comprising a set of electrodes having an anode and a cathode with an electrocatalytic surface for separation of a salt solution via electrodialysis, where the salt solution is separated into an acid stream and a basic stream, wherein at least one of (i) the basic stream of the electrodialysis unit is placed in fluid communication with the inlet of the urea decomposition unit, (ii) the acid stream from the electrodialysis unit is in fluid communication with the outlet of the urea decomposition unit, or (iii) the acid stream is circulated through the electrodialysis unit, and wherein the dialysis fluid exiting the outlet of the urea decomposition unit is cleansed dialysis fluid.

In a forty-seventh general embodiment, which may be used with the forty-sixth embodiment in combination with any other embodiment described herein unless specified otherwise, the electrodialysis unit comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane.

In a forty-eighth general embodiment, which may be used with the forty-seventh embodiment in combination with any other embodiment described herein unless specified otherwise, the first ion exchange membrane is an anion exchange membrane or a cation exchange membrane.

In a forty-ninth general embodiment, which may be used with the forty-seventh embodiment in combination with any other embodiment described herein unless specified otherwise, the second ion exchange membrane is an anion exchange membrane or a cation exchange membrane.

In a fiftieth general embodiment, which may be used with the forty-seventh embodiment in combination with any other embodiment described herein unless specified otherwise, the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

In a fifty-first general embodiment, which may be used with the fiftieth embodiment in combination with any other embodiment described herein unless specified otherwise, the first, second, and third ion exchange membranes are cation exchange membranes or the first, second, and third ion exchange membranes are anion exchange membranes.

In a fifty-second general embodiment, which may be used with the forty-sixth embodiment in combination with any other embodiment described herein unless specified otherwise, the electrodialysis unit comprises a cell including a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a fifty-third general embodiment, which may be used with the fifty-second embodiment in combination with any other embodiment described herein unless specified otherwise, the first ion exchange membrane is a cation exchange membrane and the second ion exchange membrane is an anion exchange membrane.

In a fifty-fourth general embodiment, which may be used with the forty-sixth embodiment in combination with any other embodiment described herein unless specified otherwise, a power source in the urea decomposition unit provides the electrodes with an electrical charge to activate the electrocatalytic surface of the electrodes.

In a fifty-fifth general embodiment, which may be used with the forty-sixth embodiment in combination with any other embodiment described herein unless specified otherwise, a power source in the electrodialysis unit provides the electrodes with an electrical charge to split water in a bipolar membrane into $H^+$ and $OH^-$.

In a fifty-sixth general embodiment, which may be used with the forty-sixth embodiment in combination with any other embodiment described herein unless specified otherwise, the electrodialysis unit separates the salt solution via bipolar membrane electrodialysis.

In a fifty-seventh general embodiment, which may be used with the forty-sixth embodiment in combination with any other embodiment described herein unless specified otherwise, the salt solution is a dialysis fluid.

In a fifty-eighth general embodiment, which may be used with the fifty-seventh embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a fifty-ninth general embodiment, which may be used with the forty-sixth embodiment in combination with any other embodiment described herein unless specified otherwise, the device further includes a tank for the salt solution.

In a sixtieth general embodiment, which may be used with the forty-sixth embodiment in combination with any other embodiment described herein unless specified otherwise, the basic stream includes NaOH.

In a sixty-first general embodiment, which may be used with the forty-sixth embodiment in combination with any other embodiment described herein unless specified otherwise, the acid stream includes HCl.

In a sixty-second general embodiment, which may be used with the forty-sixth embodiment in combination with any other embodiment described herein unless specified otherwise, the anodes in the urea decomposition unit comprise a transition metal and/or mixtures thereof and/or alloys thereof.

In a sixty-third general embodiment, which may be used with the sixty-second embodiment in combination with any other embodiment described herein unless specified otherwise, the transition metal is cobalt, copper, iron, nickel, platinum, palladium, iridium, ruthenium, or rhodium.

In a sixty-fourth general embodiment, which may be used with the sixty-second embodiment in combination with any other embodiment described herein unless specified otherwise, the anodes in the urea decomposition unit comprise nickel, nickel oxide, nickel hydroxide or nickel oxide hydroxide (NiOOH).

In a sixty-fifth general embodiment, which may be used with the forty-sixth embodiment in combination with any other embodiment described herein unless specified otherwise, the urea decomposition unit includes an alkaline polymeric gel.

In a sixty-sixth general embodiment, which may be used with the forty-sixth embodiment in combination with any other embodiment described herein unless specified otherwise, a voltage difference applied across the cathodes and the anodes in the urea decomposition unit is sufficient to produce nitrogen gas, carbon dioxide gas, and water.

In a sixty-seventh general embodiment, which may be used in combination with any other embodiment described herein unless specified otherwise, a method of cleaning a used dialysis fluid having urea to produce a cleansed dialysis fluid includes passing a used dialysis fluid having urea through a device. The device includes: a urea decomposition unit comprising an inlet for entry of the used dialysis fluid having urea and an outlet for removal of the cleansed dialysis fluid, and a set of electrodes having an anode and a cathode with an electrocatalytic surface for decomposition of urea via electrooxidation; and an electrodialysis unit comprising a set of electrodes having an anode and a cathode with an electrocatalytic surface for separation of a salt solution via electrodialysis, where the salt solution is separated into an acid stream and a basic stream, wherein at least one of (i) the basic stream of the electrodialysis unit is placed in fluid communication with the inlet of the urea decomposition unit, (ii) the acid stream from the electrodialysis unit is in fluid communication with the outlet of the urea decomposition unit, or (iii) the acid stream is circulated through the electrodialysis unit, and wherein the dialysis fluid exiting the outlet of the urea decomposition unit is cleansed dialysis fluid.

In a sixty-eighth general embodiment, which may be used with the sixty-seventh embodiment in combination with any other embodiment described herein unless specified otherwise, the electrodialysis unit comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane.

In a sixty-ninth general embodiment, which may be used with the sixty-eighth embodiment in combination with any other embodiment described herein unless specified otherwise, the first ion exchange membrane is an anion exchange membrane or a cation exchange membrane.

In a seventieth general embodiment, which may be used with the sixty-eighth embodiment in combination with any other embodiment described herein unless specified otherwise, the second ion exchange membrane is an anion exchange membrane or a cation exchange membrane.

In a seventy-first general embodiment, which may be used with the sixty-eighth embodiment in combination with any other embodiment described herein unless specified otherwise, the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

In a seventy-second general embodiment, which may be used with the seventy-first embodiment in combination with any other embodiment described herein unless specified otherwise, the first, second, and third ion exchange membranes are cation exchange membranes or the first, second, and third ion exchange membranes are anion exchange membranes.

In a seventy-third general embodiment, which may be used with the sixty-seventh embodiment in combination with any other embodiment described herein unless specified otherwise, the electrodialysis unit comprises a cell including a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a seventy-fourth general embodiment, which may be used with the seventy-third embodiment in combination with any other embodiment described herein unless specified otherwise, the first ion exchange membrane is a cation exchange membrane and the second ion exchange membrane is an anion exchange membrane.

In a seventy-fifth general embodiment, which may be used with the sixty-seventh embodiment in combination with any other embodiment described herein unless specified otherwise, a power source in the urea decomposition unit provides the electrodes with an electrical charge to activate the electrocatalytic surface of the electrodes.

In a seventy-sixth general embodiment, which may be used with the sixty-seventh embodiment in combination with any other embodiment described herein unless specified otherwise, a power source in the electrodialysis unit provides the electrodes with an electrical charge to split water in a bipolar membrane into $H^+$ and $OH^-$.

In a seventy-seventh general embodiment, which may be used with the sixty-seventh embodiment in combination with any other embodiment described herein unless specified otherwise, the electrodialysis unit separates the salt solution via bipolar membrane electrodialysis.

In a seventy-eighth general embodiment, which may be used with the sixty-seventh embodiment in combination with any other embodiment described herein unless specified otherwise, the salt solution is a dialysis fluid.

In a seventy-ninth general embodiment, which may be used with the seventy-eighth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In an eightieth general embodiment, which may be used with the sixty-seventh embodiment in combination with any other embodiment described herein unless specified otherwise, the device includes a tank for the salt solution.

In an eighty-first general embodiment, which may be used with the sixty-seventh embodiment in combination with any other embodiment described herein unless specified otherwise, the basic stream includes NaOH.

In an eighty-second general embodiment, which may be used with the sixty-seventh embodiment in combination with any other embodiment described herein unless specified otherwise, the acid stream includes HCl.

In an eighty-third general embodiment, which may be used with the sixty-seventh embodiment in combination with any other embodiment described herein unless specified otherwise, the anodes in the urea decomposition unit comprise a transition metal and/or mixtures thereof and/or alloys thereof.

In an eighty-fourth general embodiment, which may be used with the eighty-third embodiment in combination with any other embodiment described herein unless specified otherwise, the transition metal is cobalt, copper, iron, nickel, platinum, palladium, iridium, ruthenium, or rhodium.

In an eighty-fifth general embodiment, which may be used with the eighty-third embodiment in combination with any other embodiment described herein unless specified otherwise, the anodes in the urea decomposition unit comprise nickel, nickel oxide, nickel hydroxide or nickel oxide hydroxide (NiOOH).

In an eighty-sixth general embodiment, which may be used with the sixty-seventh embodiment in combination with any other embodiment described herein unless specified otherwise, the urea decomposition unit includes an alkaline polymeric gel.

In an eighty-seventh general embodiment, which may be used with the sixty-seventh embodiment in combination with any other embodiment described herein unless specified otherwise, a voltage difference applied across the cathodes and the anodes in the urea decomposition unit is sufficient to produce nitrogen gas, carbon dioxide gas, and water.

In an eighty-eighth general embodiment, which may be used in combination with any other embodiment described herein unless specified otherwise, a hemodialysis system that recycles a dialysis fluid includes a blood circuit and a dialysis fluid circuit, wherein the dialysis fluid circuit is in fluid communication with a device that removes urea from a used dialysis fluid having urea to produce a cleansed dialysis fluid. The device includes: a urea decomposition unit comprising an inlet for entry of the used dialysis fluid having urea and an outlet for removal of the cleansed dialysis fluid, and a set of electrodes having an anode and a cathode with an electrocatalytic surface for decomposition of urea via electrooxidation; and an electrodialysis unit comprising a set of electrodes having an anode and a cathode with an electrocatalytic surface for separation of a salt solution via electrodialysis, where the salt solution is separated into an acid stream and a basic stream, wherein at least one of (i) the basic stream of the electrodialysis unit is placed in fluid communication with the inlet of the urea decomposition unit, (ii) the acid stream from the electrodialysis unit is in fluid communication with the outlet of the urea decomposition unit, or (iii) the acid stream is circulated through the electrodialysis unit, and wherein the dialysis fluid exiting the outlet of the urea decomposition unit is cleansed dialysis fluid.

In an eighty-ninth general embodiment, which may be used with the eighty-eighth embodiment in combination with any other embodiment described herein unless specified otherwise, the electrodialysis unit comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane.

In a ninetieth general embodiment, which may be used with the eighty-ninth embodiment in combination with any other embodiment described herein unless specified otherwise, the first ion exchange membrane is an anion exchange membrane or a cation exchange membrane.

In a ninety-first general embodiment, which may be used with the eighty-ninth embodiment in combination with any other embodiment described herein unless specified otherwise, the second ion exchange membrane is an anion exchange membrane or a cation exchange membrane.

In a ninety-second general embodiment, which may be used with the eighty-ninth embodiment in combination with any other embodiment described herein unless specified otherwise, the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

In a ninety-third general embodiment, which may be used with the ninety-second embodiment in combination with any other embodiment described herein unless specified otherwise, the first, second, and third ion exchange membranes are cation exchange membranes or the first, second, and third ion exchange membranes are anion exchange membranes.

In a ninety-fourth general embodiment, which may be used with the eighty-eighth embodiment in combination with any other embodiment described herein unless specified otherwise, the electrodialysis unit comprises a cell including a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a ninety-fifth general embodiment, which may be used with the ninety-fourth embodiment in combination with any other embodiment described herein unless specified otherwise, the first ion exchange is a cation exchange membrane and the second ion exchange membrane is an anion exchange membrane.

In a ninety-sixth general embodiment, which may be used with the eighty-eighth embodiment in combination with any other embodiment described herein unless specified otherwise, a power source in the urea decomposition unit provides the electrodes with an electrical charge to activate the electrocatalytic surface of the electrodes.

In a ninety-seventh general embodiment, which may be used with the eighty-eighth embodiment in combination with any other embodiment described herein unless specified otherwise, a power source in the electrodialysis unit provides the electrodes with an electrical charge to split water in a bipolar membrane into $H^+$ and $OH^-$.

In a ninety-eighth general embodiment, which may be used with the eighty-eighth embodiment in combination with any other embodiment described herein unless specified otherwise, the electrodialysis unit separates the salt solution via bipolar membrane electrodialysis.

In a ninety-ninth general embodiment, which may be used with the eighty-eighth embodiment in combination with any other embodiment described herein unless specified otherwise, the salt solution is a dialysis fluid.

In a one-hundredth general embodiment, which may be used with the ninety-ninth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-first general embodiment, which may be used with the eighty-eighth embodiment in combination with any other embodiment described herein unless specified otherwise, the device includes a tank for the salt solution.

In a one-hundred-second general embodiment, which may be used with the eighty-eighth embodiment in combination with any other embodiment described herein unless specified otherwise, the basic stream includes NaOH.

In a one-hundred-third general embodiment, which may be used with the eighty-eighth embodiment in combination with any other embodiment described herein unless specified otherwise, the acid stream includes HCl.

In a one-hundred-fourth general embodiment, which may be used with the eighty-eighth embodiment in combination with any other embodiment described herein unless specified otherwise, the anodes in the urea decomposition unit comprise a transition metal and/or mixtures thereof and/or alloys thereof.

In a one-hundred-fifth general embodiment, which may be used with the one-hundred-fourth embodiment in combination with any other embodiment described herein unless specified otherwise, the transition metal is cobalt, copper, iron, nickel, platinum, palladium, iridium, ruthenium, or rhodium.

In a one-hundred-sixth general embodiment, which may be used with the one-hundred-fourth embodiment in combination with any other embodiment described herein unless specified otherwise, the anodes in the urea decomposition unit comprise nickel, nickel oxide, nickel hydroxide or nickel oxide hydroxide (NiOOH).

In a one-hundred-seventh general embodiment, which may be used with the eighty-eighth embodiment in combination with any other embodiment described herein unless specified otherwise, the urea decomposition unit includes an alkaline polymeric gel.

In a one-hundred-eighth general embodiment, which may be used with the eighty-eighth embodiment in combination with any other embodiment described herein unless specified otherwise, a voltage difference applied across the cathodes and the anodes in the urea decomposition unit is sufficient to produce nitrogen gas, carbon dioxide gas, and water.

In a one-hundred-ninth general embodiment, which may be used in combination with any other embodiment described herein unless specified otherwise, a device for the removal of urea from a fluid having urea to produce a cleansed fluid includes: a combination electrodialysis and urea oxidation cell including: a first set of electrodes for separation of the fluid into an acid stream and a basic stream, wherein the first set of electrodes includes an anode and a cathode; one or more second set of electrodes positioned to contact the basic stream with an electrocatalytic surface for decomposition of urea via electrooxidation; and at least one power source to provide the first and second set of electrodes with an electrical charge to activate the electrocatalytic surface.

In a one-hundred-tenth general embodiment, which may be used with the one-hundred-ninth embodiment in combination with any other embodiment described herein unless specified otherwise, the combination electrodialysis and urea oxidation cell comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane, and wherein the one or more second set of electrodes is positioned in the first compartment.

In a one-hundred-eleventh general embodiment, which may be used with the one-hundred-tenth embodiment in combination with any other embodiment described herein unless specified otherwise, the first ion exchange membrane is an anion exchange membrane or a cation exchange membrane.

In a one-hundred-twelfth general embodiment, which may be used with the one-hundred-tenth embodiment in combination with any other embodiment described herein unless specified otherwise, the second ion exchange membrane is an anion exchange membrane or a cation exchange membrane.

In a one-hundred-thirteenth general embodiment, which may be used with the one-hundred-tenth embodiment in combination with any other embodiment described herein unless specified otherwise, the combination electrodialysis and urea oxidation cell further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane, and wherein one or more third set of electrodes having an electrocatalytic surface for decomposition of urea via electrooxidation is positioned between the second ion exchange membrane and the second bipolar membrane.

In a one-hundred-fourteenth general embodiment, which may be used with the one-hundred-thirteenth embodiment in combination with any other embodiment described herein unless specified otherwise, the first, second, and third ion exchange membranes are cation exchange membranes or wherein the first, second, and third ion exchange membranes are anion exchange membranes.

In a one-hundred-fifteenth general embodiment, which may be used with the one-hundred-ninth embodiment in combination with any other embodiment described herein unless specified otherwise, the combination electrodialysis and urea oxidation cell further comprises a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a one-hundred-sixteenth general embodiment, which may be used with the one-hundred-fifteenth embodiment in combination with any other embodiment described herein unless specified otherwise, the first ion exchange membrane is a cation exchange membrane and the second ion exchange membrane is an anion exchange membrane.

In a one-hundred-seventeenth general embodiment, which may be used with the one-hundred-ninth embodiment in combination with any other embodiment described herein unless specified otherwise, the salt solution is a dialysis fluid.

In a one-hundred-eighteenth general embodiment, which may be used with the one-hundred-seventeenth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-nineteenth general embodiment, which may be used with the one-hundred-ninth embodiment in combination with any other embodiment described herein unless specified otherwise, the combination cell includes a tank for the fluid.

In a one-hundred-twentieth general embodiment, which may be used with the one-hundred-ninth embodiment in combination with any other embodiment described herein unless specified otherwise, the basic stream includes NaOH.

In a one-hundred-twenty-first general embodiment, which may be used with the one-hundred-ninth embodiment in combination with any other embodiment described herein unless specified otherwise, the acid stream includes HCl.

In a one-hundred-twenty-second general embodiment, which may be used with the one-hundred-ninth embodiment in combination with any other embodiment described herein unless specified otherwise, the anodes of the set of second electrodes comprise a transition metal and/or mixtures thereof and/or alloys thereof.

In a one-hundred-twenty-third general embodiment, which may be used with the one-hundred-twenty-second embodiment in combination with any other embodiment described herein unless specified otherwise, the transition metal is cobalt, copper, iron, nickel, platinum, palladium, iridium, ruthenium, or rhodium.

In a one-hundred-twenty-fourth general embodiment, which may be used with the one-hundred-twenty-second embodiment in combination with any other embodiment described herein unless specified otherwise, the anodes of the set of second electrodes comprise nickel, nickel oxide, nickel hydroxide or nickel oxide hydroxide (NiOOH).

In a one-hundred-twenty-fifth general embodiment, which may be used with the one-hundred-ninth embodiment in combination with any other embodiment described herein unless specified otherwise, the fluid having urea is a dialysis fluid contaminated with urea.

In a one-hundred-twenty-sixth general embodiment, which may be used with the one-hundred-ninth embodiment in combination with any other embodiment described herein unless specified otherwise, a voltage difference applied across the cathodes and the anodes in the second set of electrodes is sufficient to produce nitrogen gas, carbon dioxide gas, and water.

In a one-hundred-twenty-seventh general embodiment, which may be used in combination with any other embodiment described herein unless specified otherwise, a renal replacement therapy system includes a dialysis fluid circuit. The dialysis fluid circuit includes a combination electrodialysis and urea oxidation cell. The combination cell includes: a first set of electrodes for separation of the dialysis fluid containing urea into an acid stream and a basic stream, wherein the first set of electrodes includes an anode and a cathode; one or more second set of electrodes positioned to contact the basic stream with an electrocatalytic surface for decomposition of urea via electrooxidation; and at least one power source to provide the first and second set of electrodes with an electrical charge to activate the electrocatalytic surface.

In a one-hundred-twenty-eighth general embodiment, which may be used with the one-hundred-twenty-seventh embodiment in combination with any other embodiment described herein unless specified otherwise, the combination electrodialysis and urea oxidation cell comprises a first cell including a first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane, and wherein the one or more second set of electrodes is positioned in the first compartment.

In a one-hundred-twenty-ninth general embodiment, which may be used with the one-hundred-twenty-eighth embodiment in combination with any other embodiment described herein unless specified otherwise, the first ion exchange membrane is an anion exchange membrane or a cation exchange membrane.

In a one-hundred-thirtieth general embodiment, which may be used with the one-hundred-twenty-eighth embodiment in combination with any other embodiment described herein unless specified otherwise, the second ion exchange membrane is an anion exchange membrane or a cation exchange membrane.

In a one-hundred-thirty-first general embodiment, which may be used with the one-hundred-twenty-eighth embodiment in combination with any other embodiment described herein unless specified otherwise, the combination electrodialysis and urea oxidation cell further comprises a second cell comprising a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane, and wherein one or more third set of electrodes having an electrocatalytic surface for decomposition of urea via electrooxidation is positioned between the second ion exchange membrane and the second bipolar membrane.

In a one-hundred-thirty-second general embodiment, which may be used with the one-hundred-thirty-first embodiment in combination with any other embodiment described herein unless specified otherwise, the first, second, and third ion exchange membranes are cation exchange membranes or wherein the first, second, and third ion exchange membranes are anion exchange membranes.

In a one-hundred-thirty-third general embodiment, which may be used with the one-hundred-twenty-seventh embodiment in combination with any other embodiment described herein unless specified otherwise, the combination electrodialysis and urea oxidation cell further comprises a first bipolar membrane, a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a one-hundred-thirty-fourth general embodiment, which may be used with the one-hundred-thirty-third embodiment in combination with any other embodiment described herein unless specified otherwise, the first ion exchange membrane is a cation exchange membrane and the second ion exchange membrane is an anion exchange membrane.

In a one-hundred-thirty-fifth general embodiment, which may be used with the one-hundred-twenty-seventh embodiment in combination with any other embodiment described herein unless specified otherwise, the dialysis fluid includes a salt solution.

In a one-hundred-thirty-sixth general embodiment, which may be used with the one-hundred-twenty-seventh embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-thirty-seventh general embodiment, which may be used with the one-hundred-twenty-seventh embodiment in combination with any other embodiment described herein unless specified otherwise, the combination cell includes a tank for the dialysis fluid containing urea.

In a one-hundred-thirty-eighth general embodiment, which may be used with the one-hundred-twenty-seventh embodiment in combination with any other embodiment described herein unless specified otherwise, the basic stream includes NaOH.

In a one-hundred-thirty-ninth general embodiment, which may be used with the one-hundred-twenty-seventh embodiment in combination with any other embodiment described herein unless specified otherwise, the acid stream includes HCl.

In a one-hundred-fortieth general embodiment, which may be used with the one-hundred-twenty-seventh embodiment in combination with any other embodiment described herein unless specified otherwise, the anodes of the set of second electrodes comprise a transition metal and/or mixtures thereof and/or alloys thereof.

In a one-hundred-forty-first general embodiment, which may be used with the one-hundred-fortieth embodiment in combination with any other embodiment described herein unless specified otherwise, the transition metal is cobalt, copper, iron, nickel, platinum, palladium, iridium, ruthenium, or rhodium.

In a one-hundred-forty-second general embodiment, which may be used with the one-hundred-fortieth embodiment in combination with any other embodiment described herein unless specified otherwise, the anodes of the set of second electrodes comprise nickel, nickel oxide, nickel hydroxide or nickel oxide hydroxide (NiOOH).

In a one-hundred-forty-third general embodiment, which may be used with the one-hundred-twenty-seventh embodiment in combination with any other embodiment described herein unless specified otherwise, the combination cell includes a tank for cleansed dialysis fluid.

In a one-hundred-forty-fourth general embodiment, which may be used with the one-hundred-twenty-seventh embodiment in combination with any other embodiment described herein unless specified otherwise, a voltage difference applied across the cathode and the anode in the second set of electrodes is sufficient to produce nitrogen gas, carbon dioxide gas, and water.

In a one-hundred-forty-fifth general embodiment, which may be used in combination with any other embodiment described herein unless specified otherwise, a method of performing a renal replacement therapy includes passing a dialysis fluid having urea through a combination electrodialysis and urea oxidation cell comprising: a first set of electrodes for separation of the dialysis fluid having urea into an acid stream and a basic stream, wherein the first set of electrodes includes an anode and a cathode; one or more second set of electrodes positioned to contact the basic stream with an electrocatalytic surface for decomposition of urea via electrooxidation; and at least one power source to provide the first and second set of electrodes with an electrical charge to activate the electrocatalytic surface.

In a one-hundred-forty-sixth general embodiment, which may be used with the one-hundred-forty-fifth embodiment in combination with any other embodiment described herein unless specified otherwise, the combination electrodialysis and urea oxidation cell comprises a first cell including the first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane, and wherein the one or more second set of electrodes is positioned in the first compartment.

In a one-hundred-forty-seventh general embodiment, which may be used with the one-hundred-forty-sixth embodiment in combination with any other embodiment described herein unless specified otherwise, the first ion exchange membrane is an anion exchange membrane or a cation exchange membrane.

In a one-hundred-forty-eighth general embodiment, which may be used with the one-hundred-forty-sixth embodiment in combination with any other embodiment described herein unless specified otherwise, the second ion exchange membrane is an anion exchange membrane or a cation exchange membrane.

In a one-hundred-forty-ninth general embodiment, which may be used with the one-hundred-forty-sixth embodiment in combination with any other embodiment described herein unless specified otherwise, the combination electrodialysis and urea oxidation cell further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane, and wherein one or more third set of electrodes having an electrocatalytic surface for decomposition of urea via electrooxidation is positioned between the second ion exchange membrane and the second bipolar membrane.

In a one-hundred-fiftieth general embodiment, which may be used with the one-hundred-forty-ninth embodiment in combination with any other embodiment described herein unless specified otherwise, the first, second, and third ion exchange membranes are cation exchange membranes or the first, second, and third ion exchange membranes are anion exchange membranes.

In a one-hundred-fifty-first general embodiment, which may be used with the one-hundred-forty-fifth embodiment in combination with any other embodiment described herein unless specified otherwise, the combination electrodialysis and urea oxidation cell further comprises a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane In a one-hundred-fifty-second general embodiment, which may be used with the one-hundred-fifty-first embodiment in combination with any other embodiment described herein unless specified otherwise, the first ion exchange membrane is a cation exchange membrane and the second ion exchange membrane is an anion exchange membrane.

In a one-hundred-fifty-third general embodiment, which may be used with the one-hundred-forty-fifth embodiment in combination with any other embodiment described herein unless specified otherwise, the dialysis fluid includes a salt solution.

In a one-hundred-fifty-fourth general embodiment, which may be used with the one-hundred-forty-fifth embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-fifty-fifth general embodiment, which may be used with the one-hundred-forty-fifth embodiment in combination with any other embodiment described herein unless specified otherwise, the combination cell includes a tank for the dialysis fluid containing urea.

In a one-hundred-fifty-sixth general embodiment, which may be used with the one-hundred-forty-fifth embodiment in combination with any other embodiment described herein unless specified otherwise, the basic stream includes NaOH.

In a one-hundred-fifty-seventh general embodiment, which may be used with the one-hundred-forty-fifth embodiment in combination with any other embodiment described herein unless specified otherwise, the acid stream includes HCl.

In a one-hundred-fifty-eighth general embodiment, which may be used with the one-hundred-forty-fifth embodiment in combination with any other embodiment described herein unless specified otherwise, the anodes of the set of second electrodes comprise a transition metal and/or mixtures thereof and/or alloys thereof.

In a one-hundred-fifty-ninth general embodiment, which may be used with the one-hundred-fifty-eighth embodiment in combination with any other embodiment described herein unless specified otherwise, the transition metal is cobalt, copper, iron, nickel, platinum, palladium, iridium, ruthenium, or rhodium.

In a one-hundred-sixtieth general embodiment, which may be used with the one-hundred-fifty-eighth embodiment in combination with any other embodiment described herein unless specified otherwise, the anodes of the set of second electrodes comprise nickel, nickel oxide, nickel hydroxide or nickel oxide hydroxide (NiOOH).

In a one-hundred-sixty-first general embodiment, which may be used with the one-hundred-forty-fifth embodiment in combination with any other embodiment described herein unless specified otherwise, the combination cell includes a tank for cleansed dialysis fluid.

In a one-hundred-sixty-second general embodiment, which may be used with the one-hundred-forty-fifth embodiment in combination with any other embodiment described herein unless specified otherwise, a voltage difference applied across the cathodes and the anodes in the second set of electrodes is sufficient to produce nitrogen gas, carbon dioxide gas, and water.

In a one-hundred-sixty-third general embodiment, which may be used in combination with any other embodiment described herein unless specified otherwise, a method of cleaning a used dialysis fluid having urea to produce a clean dialysis fluid includes passing a used dialysis fluid having urea through a combination electrodialysis and urea oxidation cell. The combination cell includes a first set of electrodes for separation of the dialysis fluid having urea into an acid stream and a basic stream, wherein the first set of electrodes includes an anode and a cathode; one or more second set of electrodes positioned to contact the basic stream with an electrocatalytic surface for decomposition of urea via electrooxidation; and at least one power source to provide the first and second set of electrodes with an electrical charge to activate the electrocatalytic surface.

In a one-hundred-sixty-fourth general embodiment, which may be used with the one-hundred-sixty-third embodiment in combination with any other embodiment described herein unless specified otherwise, the combination electrodialysis and urea oxidation cell comprises a first cell including the first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane, and wherein the one or more second set of electrodes is positioned in the first compartment.

In a one-hundred-sixty-fifth general embodiment, which may be used with the one-hundred-sixty-fourth embodiment in combination with any other embodiment described herein unless specified otherwise, the first ion exchange membrane is an anion exchange membrane or a cation exchange membrane.

In a one-hundred-sixty-sixth general embodiment, which may be used with the one-hundred-sixty-fourth embodiment in combination with any other embodiment described herein unless specified otherwise, the second ion exchange membrane is an anion exchange membrane or a cation exchange membrane.

In a one-hundred-sixty-seventh general embodiment, which may be used with the one-hundred-sixty-fourth embodiment in combination with any other embodiment described herein unless specified otherwise, the combination electrodialysis and urea oxidation cell further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane, and wherein one or more third set of electrodes having an electrocatalytic surface for decomposition of urea via electrooxidation is positioned between the second ion exchange membrane and the second bipolar membrane.

In a one-hundred-sixty-eighth general embodiment, which may be used with the one-hundred-sixty-seventh embodiment in combination with any other embodiment described herein unless specified otherwise, the first, second, and third ion exchange membranes are cation exchange membranes or wherein the first, second, and third ion exchange membranes are anion exchange membranes.

In a one-hundred-sixty-ninth general embodiment, which may be used with the one-hundred-sixty-third embodiment in combination with any other embodiment described herein unless specified otherwise, the combination electrodialysis and urea oxidation cell further comprises a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a one-hundred-seventieth general embodiment, which may be used with the one-hundred-sixty-ninth embodiment in combination with any other embodiment described herein unless specified otherwise, the first ion exchange membrane is a cation exchange membrane and the second ion exchange membrane is an anion exchange membrane.

In a one-hundred-seventy-first general embodiment, which may be used with the one-hundred-sixty-third embodiment in combination with any other embodiment described herein unless specified otherwise, the dialysis fluid includes a salt solution.

In a one-hundred-seventy-second general embodiment, which may be used with the one-hundred-sixty-third embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-seventy-third general embodiment, which may be used with the one-hundred-sixty-third embodiment in combination with any other embodiment described herein unless specified otherwise, the combination cell includes a tank for the salt solution.

In a one-hundred-seventy-fourth general embodiment, which may be used with the one-hundred-sixty-third embodiment in combination with any other embodiment described herein unless specified otherwise, the basic stream includes NaOH.

In a one-hundred-seventy-fifth general embodiment, which may be used with the one-hundred-sixty-third embodiment in combination with any other embodiment described herein unless specified otherwise, the acid stream includes HCl.

In a one-hundred-seventy-sixth general embodiment, which may be used with the one-hundred-sixty-third embodiment in combination with any other embodiment described herein unless specified otherwise, the anodes of the set of second electrodes comprise a transition metal and/or mixtures thereof and/or alloys thereof.

In a one-hundred-seventy-seventh general embodiment, which may be used with the one-hundred-seventy-sixth embodiment in combination with any other embodiment described herein unless specified otherwise, the transition metal is cobalt, copper, iron, nickel, platinum, palladium, iridium, ruthenium, or rhodium.

In a one-hundred-seventy-eighth general embodiment, which may be used with the one-hundred-seventy-sixth embodiment in combination with any other embodiment described herein unless specified otherwise, the anodes of the set of second electrodes comprise nickel, nickel oxide, nickel hydroxide or nickel oxide hydroxide (NiOOH).

In a one-hundred-seventy-ninth general embodiment, which may be used with the one-hundred-sixty-third embodiment in combination with any other embodiment described herein unless specified otherwise, the combination cell includes a tank for the dialysis fluid having urea.

In a one-hundred-eightieth general embodiment, which may be used with the one-hundred-sixty-third embodiment in combination with any other embodiment described herein unless specified otherwise, a voltage difference applied across the cathodes and the anodes in the second set of electrodes is sufficient to produce nitrogen gas, carbon dioxide gas, and water.

In a one-hundred-eighty-first general embodiment, which may be used in combination with any other embodiment described herein unless specified otherwise, a hemodialysis system that recycles a dialysis fluid includes a blood circuit and a dialysis fluid circuit, wherein the dialysis fluid circuit is in fluid communication with a combination electrodialysis and urea oxidation cell comprising: a first set of electrodes with an electrocatalytic surface for separation of dialysis fluid having urea into an acid stream and a basic stream, wherein the first set of electrodes includes an anode and a cathode; one or more second set of electrodes positioned to contact the basic stream with an electrocatalytic surface for decomposition of urea via electrooxidation; and at least one power source to provide the first and second set of electrodes with an electrical charge to activate the electrocatalytic surface.

In a one-hundred-eighty-second general embodiment, which may be used with the one-hundred-eighty-first embodiment in combination with any other embodiment described herein unless specified otherwise, the combination electrodialysis and urea oxidation cell comprises a first cell including the first bipolar membrane, a first ion exchange membrane, and a second ion exchange membrane, wherein the first ion exchange membrane is positioned next to one side of the first bipolar membrane and the second ion exchange membrane is positioned next to an opposite side of the first bipolar membrane, thereby forming a first compartment between the first bipolar membrane and the first ion exchange membrane and a second compartment between the first bipolar membrane and the second ion exchange membrane, and wherein the one or more second set of electrodes is positioned in the first compartment.

In a one-hundred-eighty-third general embodiment, which may be used with the one-hundred-eighty-second embodiment in combination with any other embodiment described herein unless specified otherwise, the first ion exchange membrane is an anion exchange membrane or a cation exchange membrane.

In a one-hundred-eighty-fourth general embodiment, which may be used with the one-hundred-eighty-second embodiment in combination with any other embodiment described herein unless specified otherwise, the second ion exchange membrane is an anion exchange membrane or a cation exchange membrane.

In a one-hundred-eighty-fifth general embodiment, which may be used with the one-hundred-eighty-second embodiment in combination with any other embodiment described herein unless specified otherwise, the combination electrodialysis and urea oxidation cell further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane, and wherein one or more third set of electrodes having an electrocatalytic surface for decomposition of urea via electrooxidation is positioned between the second ion exchange membrane and the second bipolar membrane.

In a one-hundred-eighty-sixth general embodiment, which may be used with the one-hundred-eighty-fifth embodiment in combination with any other embodiment described herein unless specified otherwise, the first, second, and third ion exchange membranes are cation exchange membranes or wherein the first, second, and third ion exchange membranes are anion exchange membranes.

In a one-hundred-eighty-seventh general embodiment, which may be used with the one-hundred-eighty-first embodiment in combination with any other embodiment described herein unless specified otherwise, the combination electrodialysis and urea oxidation cell further comprises a second bipolar membrane, a first ion exchange membrane, and a second ion exchange membrane, wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

In a one-hundred-eighty-eighth general embodiment, which may be used with the one-hundred-eighty-seventh embodiment in combination with any other embodiment described herein unless specified otherwise, the first ion exchange membrane is a cation exchange membrane and the second ion exchange membrane is an anion exchange membrane.

In a one-hundred-eighty-ninth general embodiment, which may be used with the one-hundred-eighty-first embodiment in combination with any other embodiment described herein unless specified otherwise, the dialysis fluid includes a salt solution.

In a one-hundred-ninetieth general embodiment, which may be used with the one-hundred-eighty-first embodiment in combination with any other embodiment described herein unless specified otherwise, the dialysis fluid includes one or more salts selected from the group consisting of: a sodium salt, a magnesium salt, a calcium salt, lactate, carbonate, acetate, citrate, or phosphate.

In a one-hundred-ninety-first general embodiment, which may be used with the one-hundred-eighty-first embodiment in combination with any other embodiment described herein unless specified otherwise, the combination cell includes a tank for the fluid having urea.

In a one-hundred-ninety-second general embodiment, which may be used with the one-hundred-eighty-first embodiment in combination with any other embodiment described herein unless specified otherwise, the basic stream includes NaOH.

In a one-hundred-ninety-third general embodiment, which may be used with the one-hundred-eighty-first embodiment in combination with any other embodiment described herein unless specified otherwise, the acid stream includes HCl.

In a one-hundred-ninety-fourth general embodiment, which may be used with the one-hundred-eighty-first embodiment in combination with any other embodiment described herein unless specified otherwise, the anodes of the set of second electrodes comprise a transition metal and/or mixtures thereof and/or alloys thereof.

In a one-hundred-ninety-fifth general embodiment, which may be used with the one-hundred-ninety-fourth embodiment in combination with any other embodiment described herein unless specified otherwise, the transition metal is cobalt, copper, iron, nickel, platinum, palladium, iridium, ruthenium, or rhodium.

In a one-hundred-ninety-sixth general embodiment, which may be used with the one-hundred-ninety-fourth embodiment in combination with any other embodiment described herein unless specified otherwise, the anodes of the set of second electrodes comprise nickel, nickel oxide, nickel hydroxide or nickel oxide hydroxide (NiOOH).

In a one-hundred-ninety-seventh general embodiment, which may be used with the one-hundred-eighty-first embodiment in combination with any other embodiment described herein unless specified otherwise, the combination cell includes a tank for cleansed dialysis fluid.

In a one-hundred-ninety-eighth general embodiment, which may be used with the one-hundred-eighty-first embodiment in combination with any other embodiment described herein unless specified otherwise, a voltage difference applied across the cathodes and the anodes in the second set of electrodes is sufficient to produce nitrogen gas, carbon dioxide gas, and water.

In a one-hundred-ninety-ninth embodiment, which may be combined with any other embodiment discussed herein unless specified otherwise, any one, or more, or all of a controller, one or more pump, valves, pH sensors, and/or flowmeters may be employed to produce a desired flow regime.

In a two-hundredth embodiment, any of the structure, functionality and alternative embodiments associated with any of FIGS. 1 to 14 may be used with any of the structure, functionality and alternative embodiments associated with any one or more other FIGS. 1 to 14.

BRIEF DESCRIPTION OF THE FIGURES

The foregoing summary, as well as the following detailed description of the disclosure, will be better understood when read in conjunction with the appended figures. For the purpose of illustrating the disclosure, shown in the figures are embodiments which may be presently preferred. It should be understood, however, that the disclosure is not limited to the precise arrangements, examples and instrumentalities shown. Additionally, the embodiments described and claimed herein do not have to have each of the features and advantages listed herein.

DETAILED DESCRIPTION

The present disclosure provides devices and methods of using same for cleansing a solution (e.g., a salt solution) comprising urea via electrooxidation, and more specifically to cleansing a renal therapy solution/dialysis solution comprising urea via electrooxidation so that the renal therapy solution/dialysis solution can be used or reused for treatment of a patient.

Figure 1:
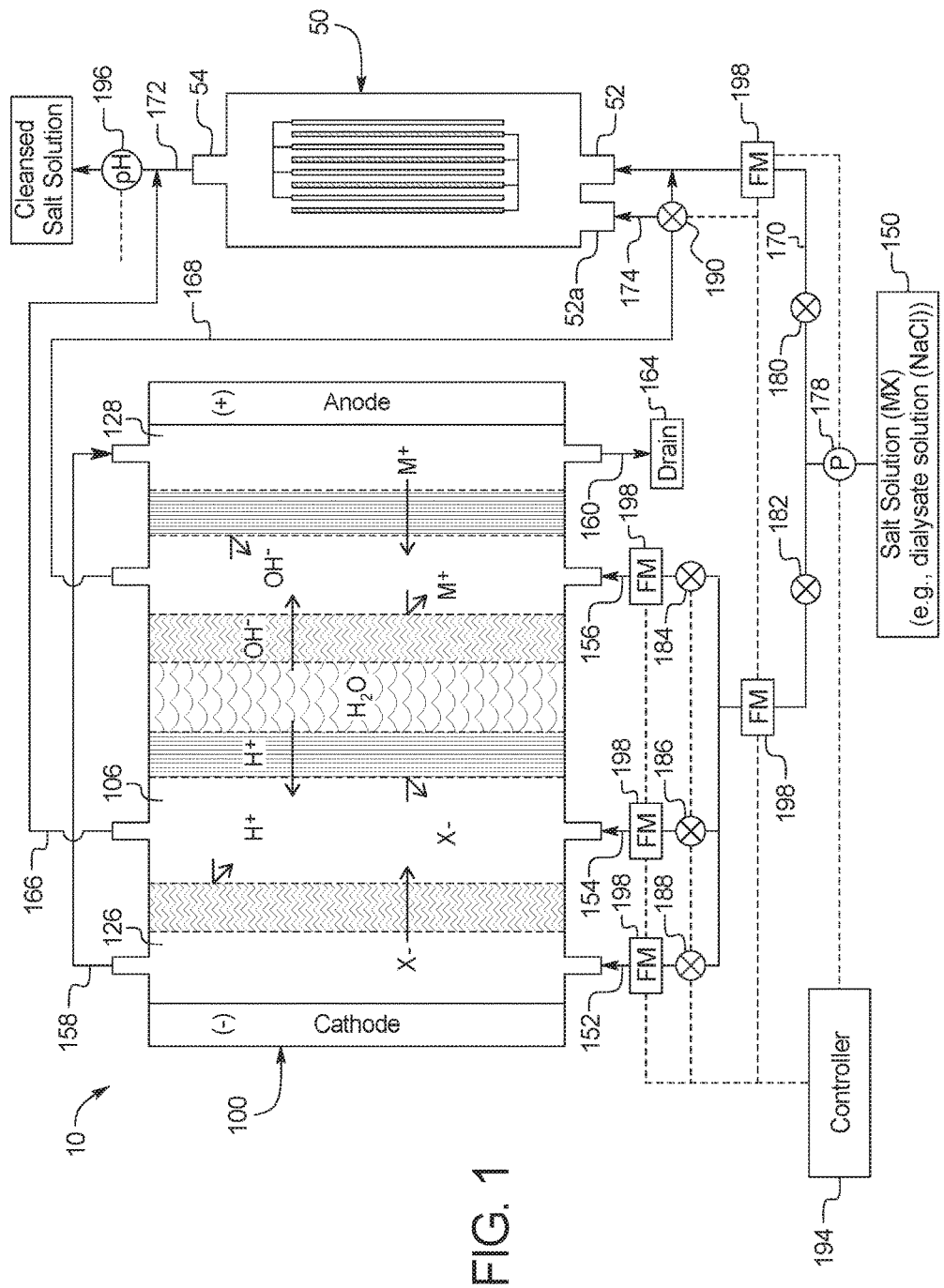
FIG. 1 shows an embodiment of a device for the removal of urea from a fluid having urea to produce a cleansed fluid.

FIG. 1 illustrates an embodiment of a device 10 for the removal of urea from a fluid having urea to produce a cleansed fluid. In the illustrated embodiment, device 10 includes a urea decomposition unit 50 and an electrodialysis unit 100. In use, and as explained in greater detail below, fluid having urea, such as dialysis fluid, can be cleansed of the urea by the combination of urea decomposition unit 50 and electrodialysis unit 100. Urea decomposition unit 50 is illustrated in more detail in FIG. 2, and electrodialysis unit 100 is illustrated in more detail in FIG. 3.

Figure 2:
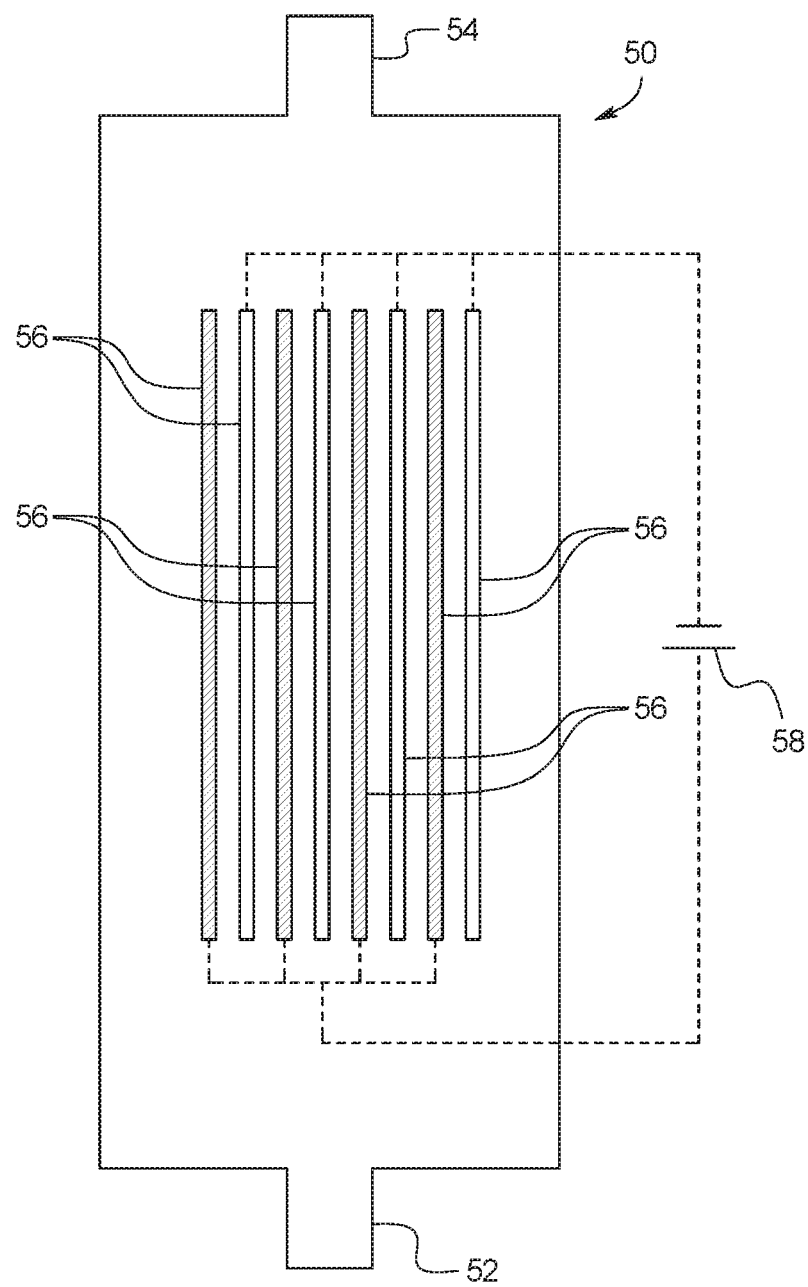
FIG. 2 shows an embodiment of a urea decomposition unit.

FIG. 2 illustrates urea decomposition unit 50, which is configured to oxidize urea into, for example, nitrogen, hydrogen, carbon dioxide and other organic byproducts, so that fluid containing urea can be cleansed of the urea. In the illustrated embodiment, urea decomposition unit 50 includes an inlet 52 for the entry of fluid having urea and an outlet 54 for the removal of cleansed fluid. Urea decomposition unit 50 can also optionally include a second inlet 52a (see FIG. 1) to receive a basic solution separate from an original salt solution to be cleansed of urea.

Urea decomposition unit 50 also includes one or more sets of electrodes 56 with electrocatalytic surfaces for the decomposition of urea via electrooxidation. Each set of electrodes 56 can include an anode and a cathode. In an embodiment, the electrodes 56 include a cathode and an anode, and the anodes comprise a transition metal and/or mixtures thereof and/or alloys thereof. The transition metal can be selected from the group consisting of cobalt, copper, iron, nickel, platinum, palladium, iridium, ruthenium, and rhodium. In an embodiment, the cathode can include platinum and the anode comprises wherein the anode comprises nickel, nickel oxide, nickel hydroxide or nickel oxide hydroxide (NiOOH). The urea decomposition unit 50 can also include an alkaline polymeric gel.

Urea decomposition unit 50 further includes a power source 58 to provide the electrodes 56 with an electrical charge. The power source 58 provides the electrodes 56 with an electrical charge to activate an electrocatalytic surface of the electrodes. The voltage difference applied across the electrodes (e.g. cathode and anode) can be sufficient to produce nitrogen gas, carbon dioxide gas, and water.

In use, fluid containing urea passes into urea decomposition unit 50 via inlet 52. The power source then charges the electrodes, which create an electrical current sufficient to oxidize the urea in the fluid into, for example, nitrogen, hydrogen, carbon dioxide and/or other organic byproducts. The fluid then exits urea decomposition unit 50 via inlet 54 as fluid without urea or a substantially reduced amount of urea (e.g., about 10%, 20%, 30%, 40%, 50%, 60%, 70%, 80%, or 90% of the amount of urea prior to entering the urea decomposition cell).

The urea decomposition unit 50 is more effective in oxidizing urea when electrooxidation is performed at a high (basic) pH including, for example, pH 8.0, 8.5, 9.0, 9.5, 10.0, 10.5, 11.0, 11.5, 12.0, 12.5, 13.0, 13.5, or 14.0. For this reason, urea decomposition unit 50 can be placed into fluid communication with an electrodialysis unit 100 that is configured to raise the pH level in the urea decomposition unit 50 and/or to raise the pH level of the fluid passing into inlet 52 and/or 52a. In an embodiment, the pH of fluid sent to urea decomposition unit 50 can be 7.1 and above, for example, from about pH 11.5 to 13.5, preferably from about pH 12.0 to 13.0.

Figure 3:
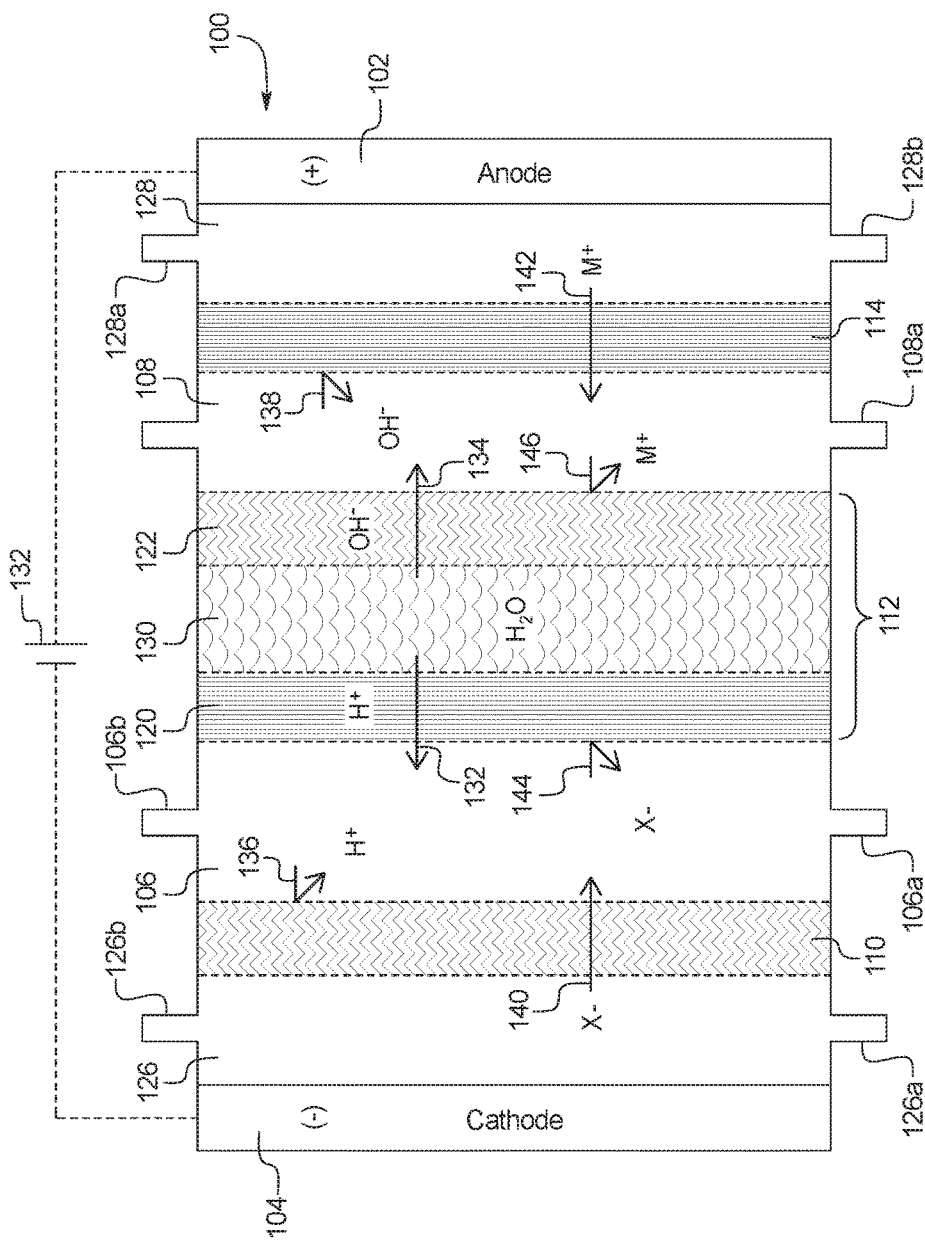
FIG. 3 shows an embodiment of an electrodialysis unit.

In the embodiment illustrated in FIG. 1, urea decomposition unit 50 is in fluid communication with an electrodialysis unit 100, as illustrated in more detail in FIG. 3. Electrodialysis unit 100 is a two-compartment electrodialysis unit including an anode 102 and a cathode 104 for separation of a salt solution via electrodialysis to generate an acid stream and a basic stream. A first compartment 106 is located between a first ion exchange membrane 110 and a bipolar membrane ("BPM") 112 and has an inlet 106a and an outlet 106b. A second compartment 108 is located between bipolar membrane 112 and a second ion exchange membrane 114 and has an inlet 108a and an outlet 108b. The cathode 104 is located on the opposite side of first ion exchange membrane 110 from first compartment 106, and the anode 102 is located on the opposite side of second ion exchange membrane 114 from second compartment 108. A cathode compartment 126 is located between cathode 104 and first ion exchange membrane 110 and has an inlet 126a and an outlet 126b. An anode compartment 128 is located between anode 102 and second ion exchange membrane 114 and has an inlet 128a and an outlet 128b. In the illustrated embodiment, the first ion exchange membrane 110 is an anion exchange membrane ("AEM") 110, and the second ion exchange membrane 114 is a cation exchange membrane ("CEM") 114. In a further embodiment, an electrodialysis unit may comprise repeats of the above-described two-compartment electrodialysis unit (i.e., [two-compartment electrodialysis unit]$_n$, where n can be any integer).

A power source 132 can create a potential difference between the anode 102 and cathode 104. The power source 132 provides an electrical potential to split water in bipolar membrane 112 into $H^+$ and $OH^-$.

Bipolar membrane 112 includes a cation exchange membrane ("CEM") 120 and an anion exchange membrane ("AEM") 122. Water can be fed into a water compartment 130 between CEM 120 and AEM 122 from a source of water (not shown). When a potential difference (e.g., a potential difference sufficient to split water) is created between the anode 102 and cathode 104, the potential difference causes water between CEM 120 and AEM 122 to split into positively charged ions (H+) and negatively charged ions (OH−) and flow through CEM 120 and AEM 122 into the first compartment 106 and second compartment 108, respectively. Specifically, positively charged ions (H+) flow through CEM 120 into first compartment 106 as illustrated by arrow 132, while negatively charged ions (OH−) flow through AEM 122 into second compartment 108 as illustrated by arrow 134. AEM 110 prevents the positively charged ions (H+) from flowing out of first compartment 106 as illustrated by arrow 136, while CEM 114 prevents the negatively charged ions (OH−) from flowing out of second compartment 108 as illustrated by arrow 138.

A salt solution can be passed through cathode compartment 126 between cathode 104 and AEM 110, and through anode compartment 128 between anode 102 and CEM 114.

In the illustrated example, the salt solution is labeled as MX. As the salt solution MX passes through cathode compartment 126 between cathode 104 and AEM 110, the potential difference (e.g., a potential difference sufficient to split the salt MX into M+ and X−) created between anode 102 and cathode 104 drives negatively charged ions (X−) through AEM 110 (toward the anode) and into first compartment 106, as illustrated by arrow 140. Similarly, as the salt solution MX passes through anode compartment 128 between anode 106 and CEM 114, the potential difference between anode 102 and cathode 104 drives positively charged ions (M+) through second ion exchange membrane 114 (toward the cathode) and into second compartment 108, as illustrated by arrow 142. CEM 120 prevents the negatively charged ions (X−) from flowing out of first compartment 106 (and into the second compartment 108) as illustrated by arrow 144, while AEM 122 prevents the positively charged ions (M+) from flowing out of second compartment 108 (and into the first compartment 106) as illustrated by arrow 146.

The potential difference created between the anode 102 and the cathode 104 is preferably sufficient to split water into positively charged ions (H+) and negatively charged ions (OH−) and split a salt MX into M+ and X−.

The potential difference created between anode 102 and cathode 104 therefore causes positively charged ions (H+) to flow through CEM 120 into first compartment 106 and causes negatively charged ions (X−) to flow through AEM 110 and into first compartment 106. The H+ and X− ions then combine in first compartment 106 to create an acidic solution (HX) with a low pH. Similarly, the potential difference created between anode 102 and cathode 104 causes negatively charged ions (OH−) flow through AEM 122 into second compartment 108 and causes positively charged ions (M+) to flow through CEM 114 and into second compartment 108. The M+ and OH− ions then combine in the second compartment 108 to create a basic solution (MOH) with a high pH.

In one example, the salt solution (MX) is sodium chloride (NaCl) (i.e., M=Na, X=Cl). The potential difference created between anode 102 and cathode 104 causes negatively charged ions (Cl−) to flow through AEM 110 and into first compartment 106, and causes positively charged ions (Na+) to flow through CEM 114 and into second compartment 108. The H+ and Cl− ions combine in first compartment 106 to create HCl, which lowers the pH of any liquid in first compartment 106. The Na+ and OH− ions combine in second compartment 108 to create NaOH. In other embodiment, the salt solution can include one or more salts selected from the group consisting of: a sodium salt, a magnesium salt, a calcium salt, lactate, carbonate, acetate, citrate, and phosphate. In another embodiment, source 150 can include used dialysis fluid/renal therapy solution that is in need of regeneration for further renal failure therapy.

Returning to FIG. 1, an example device 10 is illustrated to show how urea decomposition unit 50 can be placed in fluid communication with electrodialysis unit 100. First, a source of salt solution 150 (represented in FIG. 1 by "MX") containing urea can be placed in fluid communication with one or more of first compartment 106, second compartment 108, cathode compartment 126 and/or anode compartment 128. In the illustrated embodiment, the source of fluid 150 is placed into fluid communication with the respective inlets 126a, 106a and 108a of cathode compartment 126, first compartment 106 and second compartment 108, as illustrated by flowpaths (arrows) 152, 154 and 156. As illustrated by flowpath (arrow) 158, the salt solution that flows into cathode compartment 126 loses negatively charged ions (X−) to first compartment 106 and is then circulated to anode compartment 128, where it loses positively charged ions (M+) to second compartment 108. As illustrated by flowpath (arrow) 160, the salt solution circulated through cathode compartment 126 and anode compartment 128 can then be sent to drain 164 as waste fluid.

Referring to FIGS. 1 and 3, the salt solution (MX) that flows from inlet 106a to outlet 106b of first compartment 106 is combined with the acid solution (HX) that has been formed in first compartment 106 as described above, which lowers the pH of the salt solution (MX) flowing through first compartment 106. Likewise, the salt solution (MX) that flows from inlet 108a to outlet 108b of second compartment 108 is combined with the base solution (MOH) that has been formed in second compartment 108 as described above, which increases the pH of the salt solution (MX) flowing through second compartment 108. Electrodialysis unit 100 therefore produces an outflow of an acidic salt solution (represented at flowpath 166 leaving outlet 106b) and an outflow of a base salt solution (represented at flowpath 168 leaving outlet 108b).

As illustrated by flowpath 170, a large portion of the original urea-containing salt solution (MX) can be sent directly to urea decomposition unit 50 without passing through electrodialysis unit 100. In the illustrated embodiment, approximately 94% of the salt solution flows directly to urea decomposition unit 50 without passing through electrodialysis unit 100. The original salt solution (MX) is combined with the base solution (MOH) created by electrodialysis unit 100 (illustrated by flowpath 168) to raise the pH of the combined salt solution entering inlet 52 of urea decomposition unit 50. As explained above, it has been demonstrated that urea decomposition unit 50 is more effective in oxidizing urea when fluid entering inlet 52 is basic (alkaline) as opposed to acidic. In one embodiment, the base solution (MOH) flowing through flowpath 168 can mix with original salt solution flowing through flowpath 170 before the mixed salt solution flows into inlet 52 of urea decomposition unit 50. In another embodiment, the base solution (MOH) flowing through flowpath 168 can flow into a separate inlet 52a of urea decomposition unit 50 through flowpath 174 and mix with original salt solution that has already flowed through inlet 52.

After the combined salt solution has been cleansed of urea, the outflow of acidic solution (represented at flowpath 166) is added to the outflow of combined solution from outlet 54 (represented at flowpath 172) of urea decomposition unit 50 so that the pH of the combined salt solution after intersection of flowpaths 166 and 172 is lowered back to normal (e.g. a physiological pH such as a pH of about 7.0). The combined solution can then be sent to a dialysis fluid equalization unit 28, as described below. The low pH acidic solution (HX) can also be used to clean the cells in the urea decomposition unit 50 and/or electrodialysis unit 100 after operation.

In use, the majority of salt solution from source 150 is output from source 150 at flowpath 170. In an embodiment, the source of salt solution 150 outputs about 405 mL/min of salt solution. 380 mL/min is directed to urea decomposition unit 50 along flowpath 170, 5 mL/min is directed to cathode compartment 126 and anode compartment 128 along flowpaths 152, 158 and 160, 10 mL/min is directed through first compartment 106 along flowpath 154, and 10 mL/min is directed through second compartment 108 along flowpath 156. Thus, 96% of the salt solution entering urea decomposition unit 50 via flowpaths 168 and 170, and 97.5% of the cleansed solution after the combination of flowpaths 166 and 172, is cleansed of urea via electrooxidation.

It is preferable to keep the amount of fluid sent to electrodialysis unit 100 as low as possible, because less fluid is oxidized of urea by urea decomposition unit 50 as more fluid is sent to cathode compartment 126 and first compartment 106. In an embodiment, approximately 70 to 95% of the total solution from source 150 passes along flowpath 170 directly to urea decomposition unit 50, while the remaining 5 to 30% of the total solution from source 150 passes along flowpaths 152, 154 and 156 to electrodialysis unit 100. In another embodiment, the source of salt solution 150 outputs about 100 to 600 mL/min of salt solution. 70% to 100% of the salt solution is directed to urea decomposition unit 50 along flowpath 170, and 0% to 30% of the total solution from source 150 passes along flowpaths 152, 154 and 156 to electrodialysis unit 100.

In another embodiment, source 150 contains sodium chloride (NaCl) at 0.132 mol/L (pH 7.0) and outputs about 400 mL/min of solution. 30 mL/min flows through cathode compartment 126 and anode compartment 128 along flowpaths 152, 158 and 160. 5 mL/min flows through first compartment 106 along flowpath 154, which causes first compartment 106 to output solution with 0.792 mol/L of HCL (pH 0.1) at flowpath 166. 5 mL/min also flows through second compartment 108 along flowpath 156, which causes second compartment 108 to output solution with 0.792 mol/L of NaOH (pH 13.9) at flowpath 168. The remaining 360 mL/min from the total 400 mL/min output by source 150 is directed along flowpath 170. When flowpaths 170 and 168 combine, the combined solution has an NaOH concentration of 0.0108 mol/L (ph 12.04) as it enters inlet 52 of urea decomposition unit 50.

In an embodiment, dialysis fluid with salt solution (NaCl) achieves a pH of about 13.1 at urea decomposition unit 50 (0.132 mol/L NaCl converted into 0.132 mol/L NaOH=pH 13.1). A pH of 13.1 is a best case scenario for dialysis fluid solution in which 100% of the dialysis fluid solution is sent directly to the electrodialysis unit 100, and then the basic feed is sent to the urea decomposition unit 50.

FIG. 1 illustrates that in an embodiment, device 10 may include one or more pump 178, and a plurality of valves 180, 182, 184, 186, 188, 190 that control fluid flow along the respective flowpaths. Pump 178 may be a peristaltic pump or a volume membrane pump. The valves 180, 182, 184, 186, 188, 190 may be variable fluid orifice valves that allow a percentage of fluid to flow through each respective flowpath. Alternatively, the valves can be solenoid valves or other valves known to those of ordinary skill in the art. In the illustrated embodiment, the valves 180, 182, 184, 186, 188, 190 are electrically connected to a controller 194. The controller 194 may include one or more processor and memory programmed to control one or more pump 178 and the variable orifice size of valves 180, 182, 184, 186, 188, 190 to achieve the flow rates and percentages discussed above or to achieve other flowrates and percentages through the respective flowpaths.

In an embodiment, any one or more or all of valves 180, 182, 184, 186, 188, 190 may alternatively be solenoid valves that operate with controller 194 so that they are opened a specified amount of time to achieve the flow distributions through device 10 described above. In a further embodiment, one or more valves, such as valves 180, 182, 184, 186, 188, 190, may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 194 can precisely meter fluid through the flowpaths by toggling the solenoid valves of the balance chamber between the first compartment and the second compartment and control flow rate by controlling how often the inlet and outlet valves are cycled.

In an embodiment, device 10 includes a pH sensor 196 that ensures the pH of the cleansed salt solution is at or near 7.0 (i.e., neutral). The pH sensor 196 may provide feedback to controller 194, so that controller 194 controls pump 178 and/or valves 180, 182, 184, 186, 188, 190 to raise or lower the pH of the outflow as necessary. Device 10 may also include one or more flowmeters (FM) 198 to monitor flow at any desired one or more location within the respective flowpaths of device 10 and provide flowrate feedback to controller 194.

Figure 4:
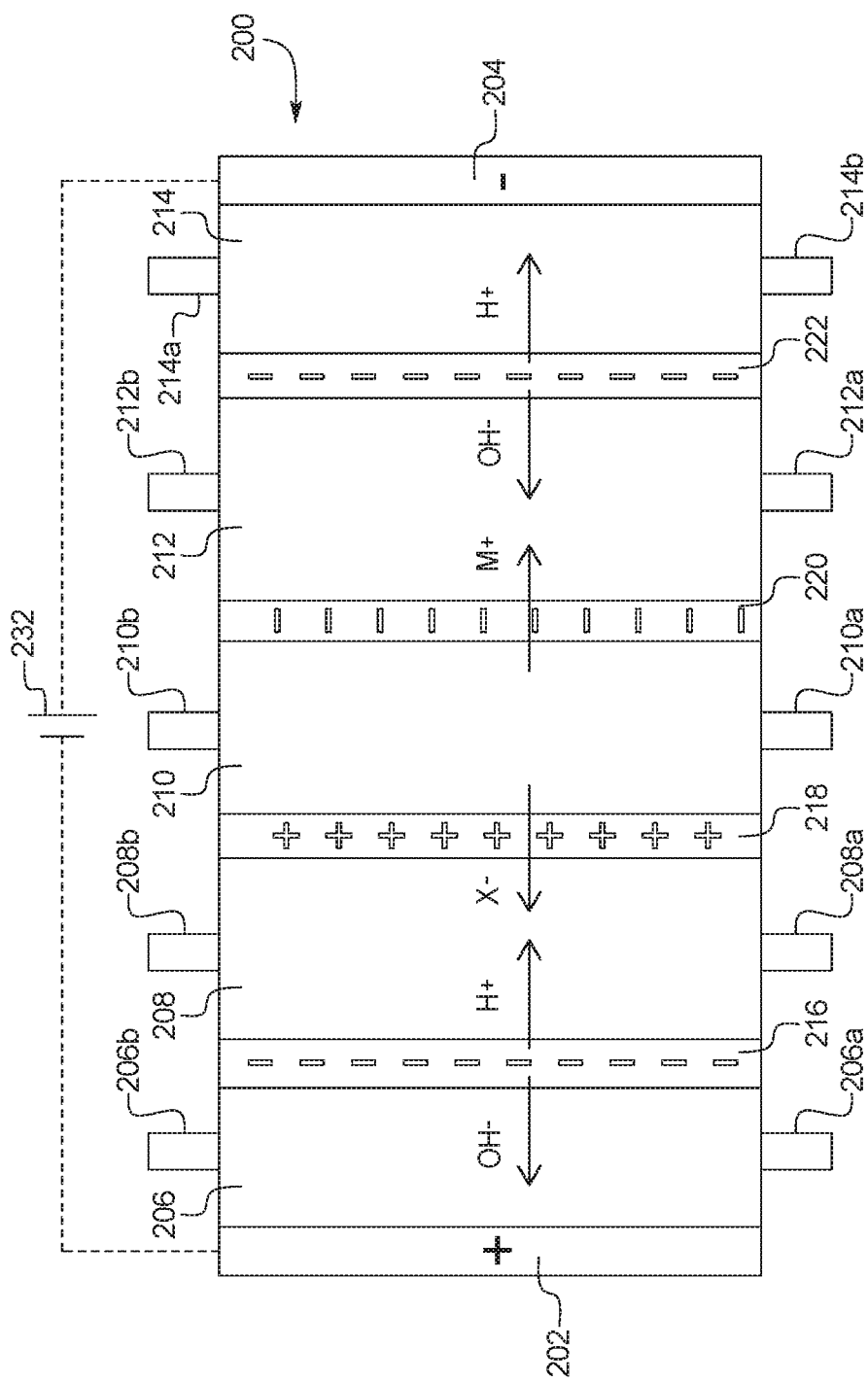
FIG. 4 shows an alternative embodiment of an electrodialysis unit.

FIG. 4 illustrates an example embodiment of another electrodialysis unit 200 that can be combined with urea decomposition unit 50 to cleanse a salt solution of urea. Electrodialysis unit 200 is a three-compartment electrodialysis unit including an anode 202 and a cathode 204 for separation of a salt solution via electrodialysis. Similar to above, electrodialysis unit 200 includes an anode compartment 206 located between anode 202 and a bipolar membrane 216 and including an inlet 206a and an outlet 206b, a first compartment 208 located between bipolar membrane 216 and a first ion exchange membrane 218 (here AEM 218) and including an inlet 208a and an outlet 208b, a second compartment 210 located between AEM 218 and a second ion exchange membrane 220 (here CEM 220) and including an inlet 210a and an outlet 210b, a third compartment 212 located between CEM 220 and a bipolar membrane 222 and including an inlet 212a and an outlet 212b, and a cathode compartment 214 located between bipolar membrane 222 and cathode 204 and including an inlet 214a and an outlet 214b. In a further embodiment, an electrodialysis unit may comprise repeats of the above-described three-compartment electrodialysis unit (i.e., [three-compartment electrodialysis unit]$_n$, where n can be any integer).

A power source 232 can create a potential difference between the anode 202 and cathode 204. The power source 232 provides an electrical potential to split water in bipolar membranes 216 and 222 into $H^+$ and $OH^-$.

Bipolar membranes 216 and 222 each include a CEM and an AEM as described above with respect to bipolar membrane 112. For each bipolar membrane 216 and 222, water can be fed into a water compartment between the CEM and AEM from a source of water. For simplicity, the water compartment, CEM and AEM are not shown separately in FIG. 4. When a potential difference (e.g., a potential difference sufficient to split water) is created between the anode 202 and cathode 204, the potential difference causes water to split into positively charged ions (H+) and negatively charged ions (OH−) in bipolar membrane 216. The generated negatively charged ions (OH−) from bipolar membrane 216 flow through the AEM and into cathode compartment 206, and the generated positively charged ions (H+) flow through the CEM and into first compartment 208. Similarly, the potential difference causes the negatively charged ions (OH−) generated in the bipolar membrane 222 to flow through the AEM and into third compartment 212, and the positively charged ions (H+) to flow through the CEM and into cathode compartment 214.

Figure 5:
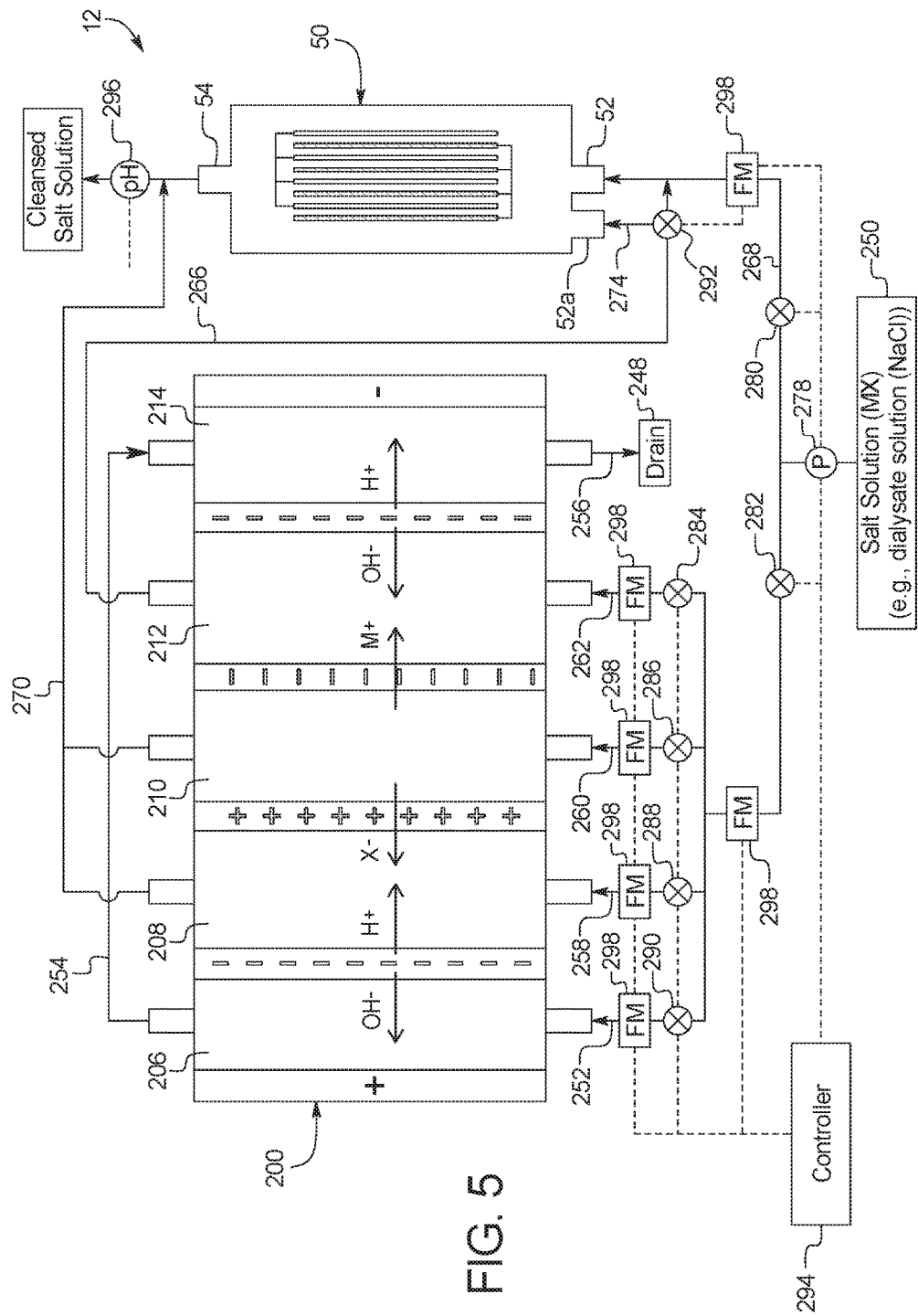
FIG. 5 shows an alternative embodiment of a device for the removal of urea from a fluid having urea to produce a cleansed fluid.

FIG. 5 shows a device 12 placing electrodialysis unit 200 in fluid communication with the urea decomposition unit 50 of FIG. 2. As shown by flowpaths 252, 254 and 256, salt solution (MX) from a source 250 can be passed through anode compartment 206 and cathode compartment 214 and sent to drain 248 as described above. The salt solution can also be passed through each of first compartment 208 (flowpath 258), second compartment 210 (flowpath 260) and third compartment 212 (flowpath 262). As salt solution passes through second compartment 210, the potential difference created between the anode 202 and cathode 204 drives negatively charged ions (X−) through AEM 218 and into first compartment 208. Likewise, the potential difference created between the anode 202 and cathode 204 drives positively charged ions (M+) through CEM 220 and into third compartment 212. The CEM of bipolar membrane 216 prevents the negatively charged ions (X−) from flowing out of first compartment 208, while the AEM of bipolar membrane 222 prevents the positively charged ions (M+) from flowing out of third compartment 212.

The potential difference created between anode 202 and cathode 204 therefore causes positively charged ions (H+) and negatively charged ions (X−) in first compartment 208 to create an acidic solution (HX) with a low pH. Similarly, the potential difference created between anode 202 and cathode 204 causes negatively charged ions (OH−) and positively charged ions (M+) in third compartment 212 to create a basic solution (MOH) with a high pH.

Similar to above, flowpaths 266 and 268 illustrate that urea decomposition unit 50 can be placed in fluid communication with electrodialysis unit 200 so that the high pH basic solution (MOH) can be combined with an original salt solution 250 containing urea to raise the pH of the original salt solution prior to entering urea decomposition unit 50. In one embodiment, the basic solution (MOH) flowing through flowpath 266 can mix with original salt solution flowing through flowpath 268 before the mixed salt solution flows into inlet 52 of urea decomposition unit 50. In another embodiment, the base solution (MOH) flowing through flowpath 266 can flow into a separate inlet 52a of urea decomposition unit 50 through flowpath 274 and mix with original salt solution that has already flowed through inlet 52.

The low pH acidic solution (HX) can then be combined with outflow from urea decomposition unit 50 so that the pH of the combined salt solution is lowered back to normal (e.g., a physiological pH such as a pH of about 7.0), as illustrated by flowpath 270. The combined solution can then be sent to a dialysis fluid equalization unit 28, as described below. The low pH acidic solution (HX) can also be used to clean the cells in the urea decomposition unit 50 and/or electrodialysis unit 200 after operation.

In an embodiment, approximately 70 to 90% of the total solution from source 250 passes along flowpath 268 directly to urea decomposition unit 50, while the remaining 10 to 30% of the total solution from source 250 passes along flowpaths 252, 258, 260 and 262 to electrodialysis unit 200.

FIG. 5 illustrates that in an embodiment, device 12 may include one or more pump 278, and a plurality of valves 280, 282, 284, 286, 288, 290, 292 that control fluid flow along the respective flowpaths. Pump 278 may be a peristaltic pump or a volume membrane pump. The valves 280, 282, 284, 286, 288, 290, 292 may be variable fluid orifice valves that allow a percentage of fluid to flow through each respective flowpath. Alternatively, the valves can be solenoid valves or other valves known to those of ordinary skill in the art. In the illustrated embodiment, the valves 280, 282, 284, 286, 288, 290, 292 are electrically connected to a controller 294. The controller 294 may include one or more processor and memory programmed to control one or more pump 278 and the variable orifice size of valves 280, 282, 284, 286, 288, 290, 292 to achieve the flow rates and percentages discussed above or to achieve other flowrates and percentages through the respective flowpaths.

In an embodiment, any one or more or all of valves 280, 282, 284, 286, 288, 290, 292 may alternatively be solenoid valves that operate with controller 294 so that they are opened a specified amount of time to achieve the flow distributions through device 12 described above. In a further embodiment, one or more valves, such as valves 280, 282, 284, 286, 288, 290, 292, may be replaced with a balance chamber that operates with its own valves Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 294 can precisely meter fluid through the flowpaths by toggling the solenoid valves of the balance chamber between the first compartment and the second compartment and control flow rate by controlling how often the inlet and outlet valves are cycled.

In an embodiment, device 12 includes a pH sensor 296 that ensures the pH of the cleansed salt solution is at or near 7.0 (i.e., neutral). The pH sensor 296 may provide feedback to controller 294, so that controller 294 controls pump 278 and/or valves 280, 282, 284, 286, 288, 290, 292 to raise or lower the pH of the outflow as necessary. Device 12 may also include one or more flowmeters (FM) 298 to monitor flow at any desired one or more location within the respective flowpaths of device 12 and provide flowrate feedback to controller 294.

Figure 6:
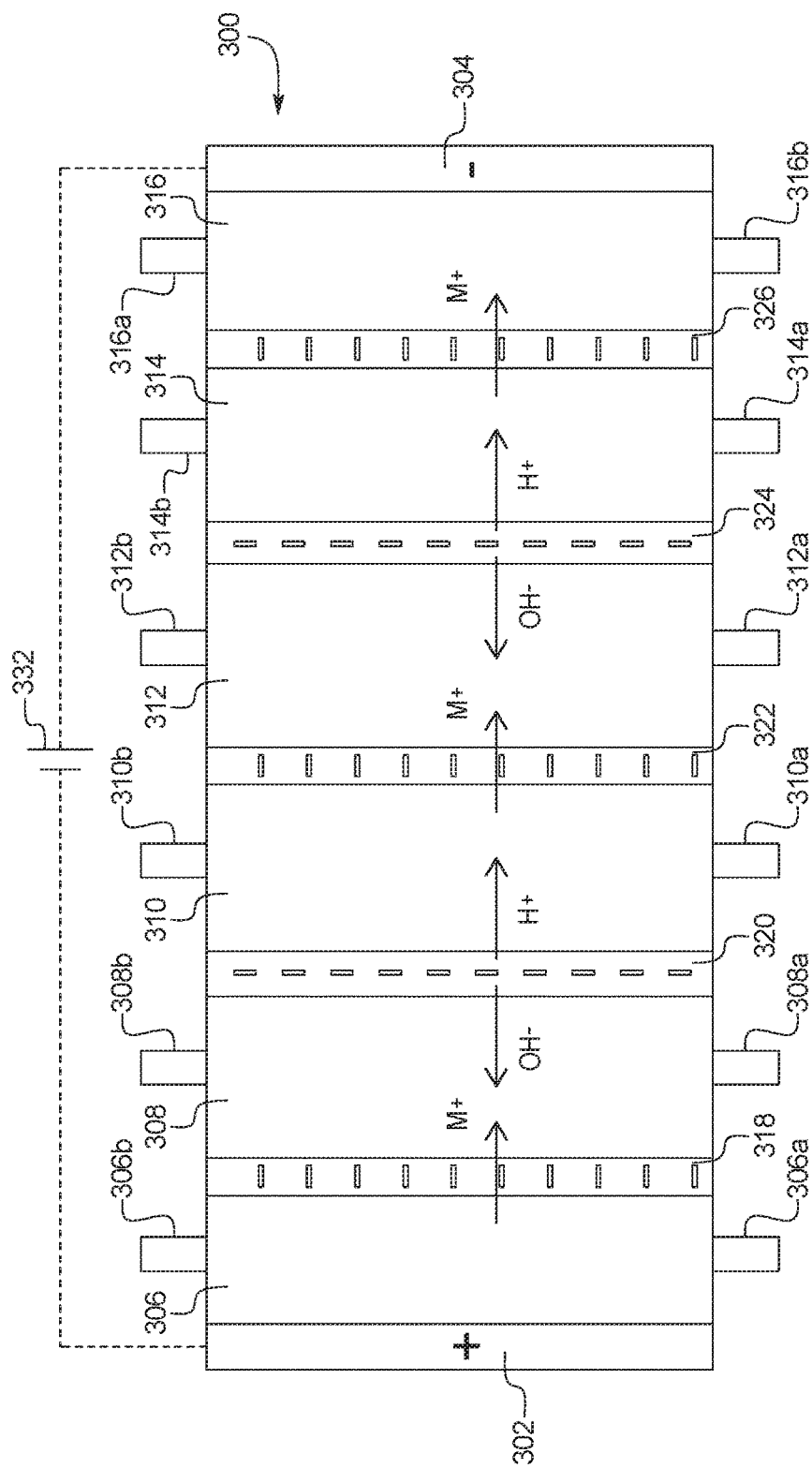
FIG. 6 shows an alternative embodiment of an electrodialysis unit.

FIG. 6 illustrates an embodiment of another electrodialysis unit 300 that can be combined with urea decomposition unit 50 to cleanse a salt solution of urea. Electrodialysis unit 300 is a two-compartment, two-cell electrodialysis unit including an anode 302 and a cathode 304 for separation of a salt solution via electrodialysis. Similar to above, electrodialysis unit 300 includes an anode compartment 306 located between anode 302 and a first ion exchange membrane 318 and including an inlet 306a and an outlet 306b, a first compartment 308 located between first ion exchange membrane 318 and a bipolar membrane 320 and including an inlet 308a and an outlet 308b, a second compartment 310 located between bipolar membrane 320 and a second ion exchange membrane 322 and including an inlet 310a and an outlet 310b, a third compartment 312 located between second ion exchange membrane 322 and a bipolar membrane 324 and including an inlet 312a and an outlet 312b, a fourth compartment 314 located between bipolar membrane 324 and a third ion exchange membrane 326 and including an inlet 314a and an outlet 314b, and a cathode compartment 316 located between third ion exchange membrane 326 and cathode 304 and including an inlet 316a and an outlet 316b.

In the illustrated embodiment, the first ion exchange membrane 318, second ion exchange membrane 322 and third ion exchange membrane 326 are each a CEM.

A power source 332 can create a potential difference between the anode 302 and cathode 304. The power source 332 provides an electrical potential to split water in bipolar membranes 320 and 324 into $H^+$ and $OH^-$.

Bipolar membranes 320 and 324 each include a CEM and an AEM as described above with respect to bipolar membrane 112. For each bipolar membrane 320 and 324, water can be fed into a water compartment between the CEM and AEM from a source of water. For simplicity, the water compartment, CEM and AEM are not shown separately in FIG. 6. When a potential difference (e.g., a potential difference sufficient to split water) is created between the anode 302 and cathode 304, the potential difference causes water to split into positively charged ions (H+) and negatively charged ions (OH−). The generated negatively charged ions (OH−) from bipolar membrane 320 flow through the AEM and into first compartment 308, and the generated positively charged ions (H+) flow through the CEM and into second compartment 310. Similarly, the potential difference causes the negatively charged ions (OH−) from bipolar membrane 324 to flow through the AEM and into third compartment 312, and causes the positively charged ions (H+) to flow through the CEM and into fourth compartment 314.

Figure 7:
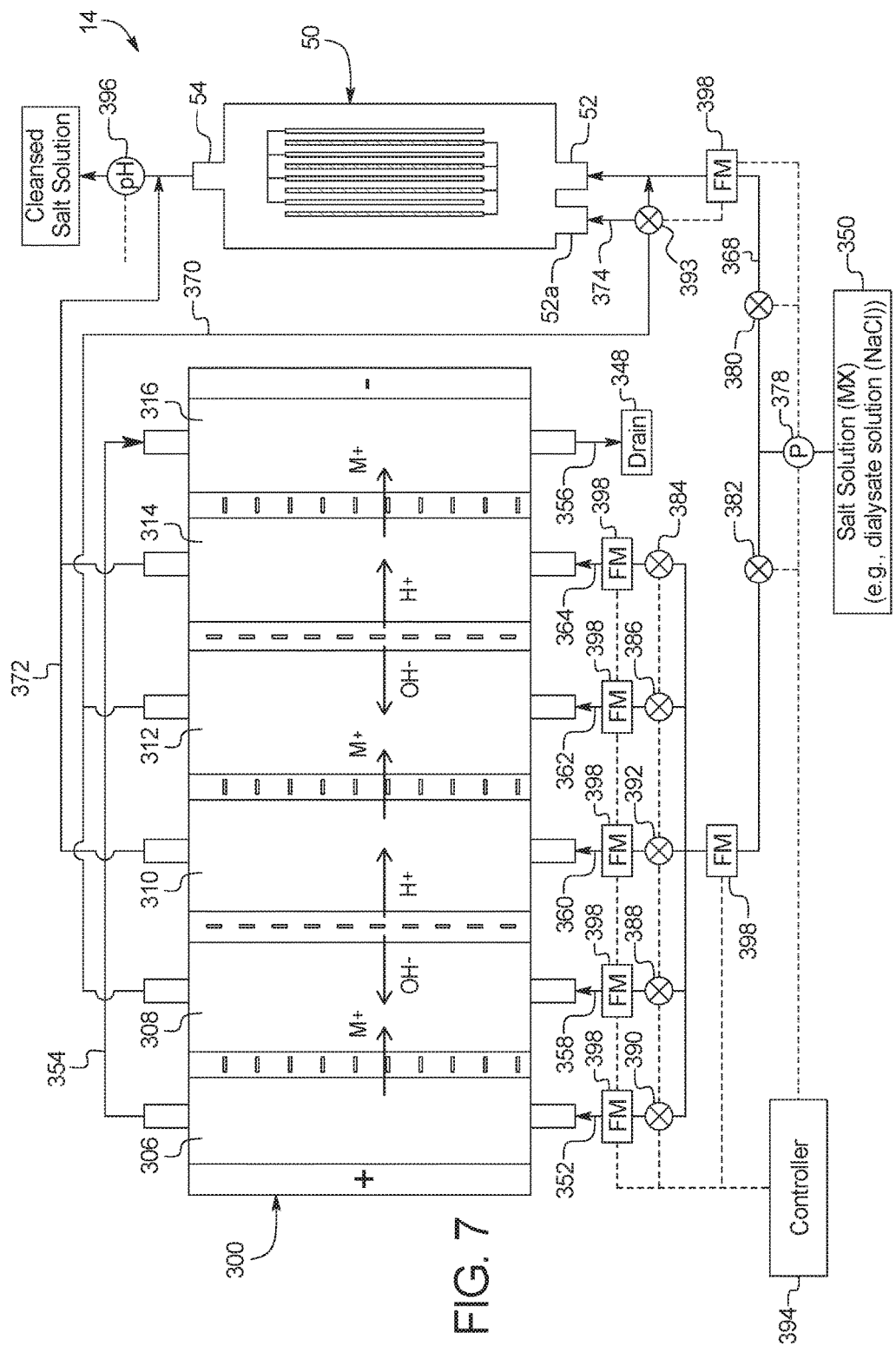
FIG. 7 shows an alternative embodiment of a device for the removal of urea from a fluid having urea to produce a cleansed fluid.

FIG. 7 shows a device 14 placing electrodialysis unit 300 in fluid communication with the urea decomposition unit 50 of FIG. 2. As shown by flowpaths 352, 354 and 356, salt solution (MX) from a source 350 can be passed through anode compartment 306 and cathode compartment 316 and sent to drain 348 as described above. A salt solution can also be passed through each of first compartment 308 (flowpath 358), second compartment 310 (flowpath 360), third compartment 312 (flowpath 362) and fourth compartment 314 (flowpath 364). In the illustrated embodiment, first ion exchange membrane 318 is a first CEM 318, second ion exchange membrane 322 is a second CEM 322, and third ion exchange membrane 326 is a third CEM 326. Salt solution (MX) passing through anode compartment 306 therefore loses positively charged ions (M+) through CEM 318 to first compartment 308, salt solution passing through second compartment 310 loses positively charged ions (M+) through CEM 322 to third compartment 312, and salt solution passing through fourth compartment 314 loses positively charged ions (M+) through CEM 326 to cathode compartment 316. The AEM of bipolar membrane 320 prevents the positively charged ions (M+) from flowing out of first compartment 308, while the AEM of bipolar membrane 324 prevents the positively charged ions (M+) from flowing out of third compartment 312.

The potential difference created between anode 302 and cathode 304 causes negatively charged ions (OH−) and positively charged ions (M+) to form a basic solution (MOH) with a high pH in first compartment 308 and third compartment 312. Similar to above, flowpaths 368 and 370 illustrate that urea decomposition unit 50 can be placed in fluid communication with electrodialysis unit 300 so that the high pH basic solution (MOH) from first compartment 308 and third compartment 312 can be combined with original salt solution containing urea to raise the pH of the original salt solution prior to entering urea decomposition unit 50. In one embodiment, the basic solution (MOH) flowing through flowpath 370 can mix with original salt solution flowing through flowpath 368 before the mixed salt solution flows into inlet 52 of urea decomposition unit 50. In another embodiment, the base solution (MOH) flowing through flowpath 370 can flow into a separate inlet 52a of urea decomposition unit 50 through flowpath 374 and mix with original salt solution that has already flowed through inlet 52.

Low pH acidic solution can then be combined with outflow from urea decomposition unit 50 so that the pH of the combined salt solution is lowered back to normal, as illustrated by flowpath 372. The combined solution can then be sent to a dialysis fluid equalization unit 28, as described below. The low pH acidic solution can also be used to clean the cells in the urea decomposition unit 50 and/or electrodialysis unit 300 after operation.

In an embodiment, approximately 70 to 95% of the total solution from source 350 passes along flowpath 368 directly to urea decomposition unit 50, while the remaining 5 to 30% of the total solution from source 350 passes along flowpaths 352, 360, 362, 364 and 366 to electrodialysis unit 300.

FIG. 7 illustrates that in an embodiment, device 14 may include one or more pumps 378, and a plurality of valves 380, 382, 384, 386, 388, 390, 392, 393 that control fluid flow along the respective flowpaths. Pump 378 may be a peristaltic pump or a volume membrane pump. The valves 380, 382, 384, 386, 388, 390, 392, 393 may be variable fluid orifice valves that allow a percentage of fluid to flow through each respective flowpath. Alternatively, the valves can be solenoid valves or other valves known to those of ordinary skill in the art. In the illustrated embodiment, the valves 380, 382, 384, 386, 388, 390, 392, 393 are electrically connected to a controller 394. The controller 394 may include one or more processor and memory programmed to control one or more pump 378 and the variable orifice size of valves 380, 382, 384, 386, 388, 390, 392, 393 to achieve the flow rates and percentages discussed above or to achieve other flowrates and percentages through the respective flowpaths.

In an embodiment, any one or more or all of valves 380, 382, 384, 386, 388, 390, 392, 393 may alternatively be solenoid valves that operate with controller 394 so that they are opened a specified amount of time to achieve the flow distributions through device 14 described above. In a further embodiment, one or more valves, such as valves 380, 382, 384, 386, 388, 390, 392, 393, may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 394 can precisely meter fluid through the flowpaths by toggling the solenoid valves of the balance chamber between the first compartment and the second compartment and control flow rate by controlling how often the inlet and outlet valves are cycled.

In an embodiment, device 14 includes a pH sensor 396 that ensures the pH of the cleansed salt solution is at or near 7.0 (i.e., neutral). The pH sensor 396 may provide feedback to controller 394, so that controller 394 controls pump 378 and/or valves 380, 382, 384, 386, 388, 390, 392, 393 to raise or lower the pH of the outflow as necessary. Device 14 may also include one or more flowmeters (FM) 398 to monitor flow at any desired one or more location within the respective flowpaths of device 14 and provide flowrate feedback to controller 394.

Figure 8:
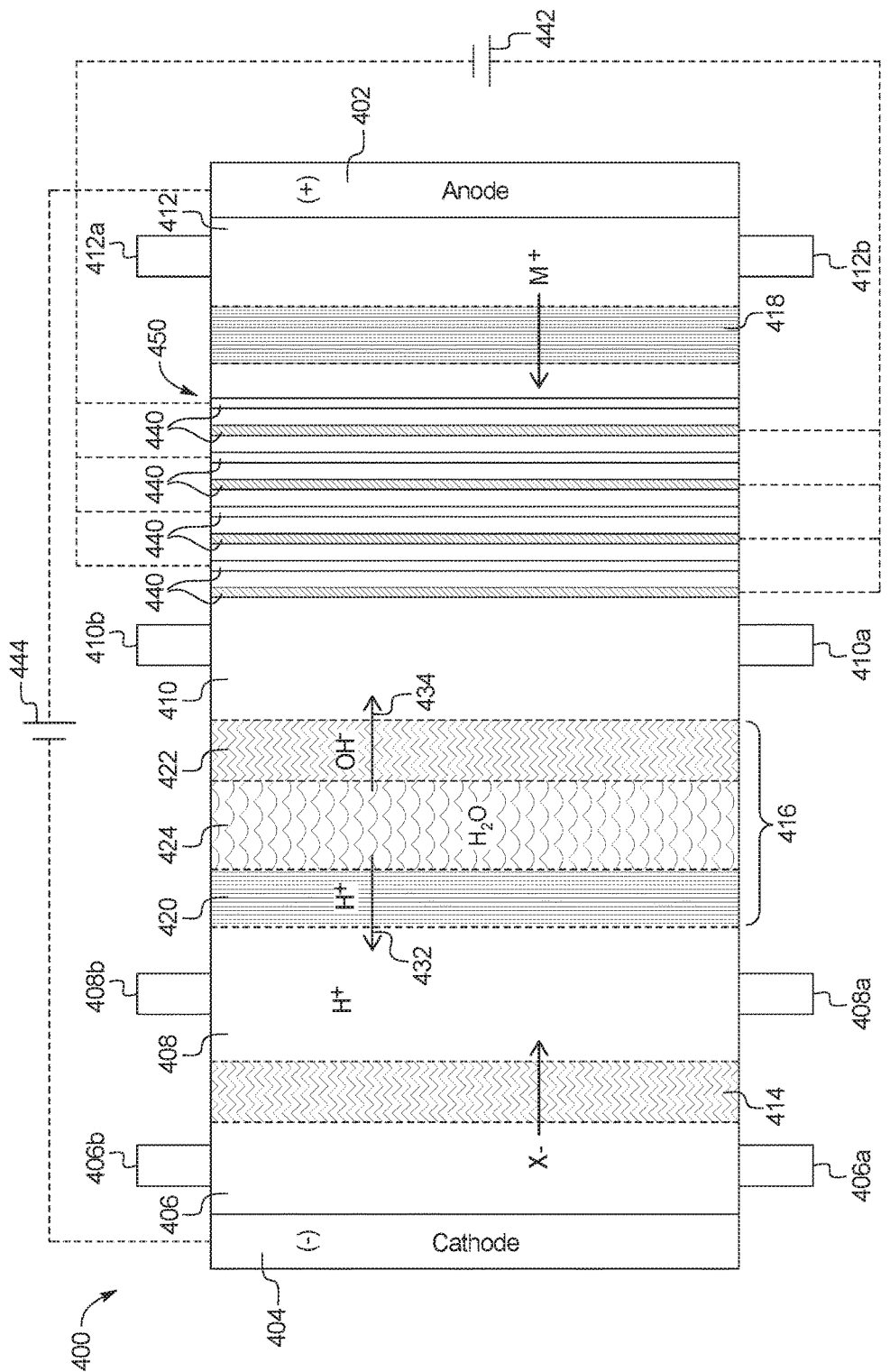
FIG. 8 shows an alternative embodiment of a device for the removal of urea from a fluid having urea to produce a cleansed fluid.

FIG. 8 illustrates a device 400 that combines the urea decomposition and electrodialysis units discussed above into the same unit. More specifically, device 400 take the electrodes from urea decomposition unit 50 and places the electrodes inside of one or more compartment of electrodialysis unit 100, 200, 300. The oxidation of urea from salt solution therefore occurs inside of the compartment due to the electrocatalytic surfaces of the electrodes for decomposition of urea via electrooxidation.

Similar to above, device 400 includes a cathode compartment 406 located between a cathode 404 and a first ion exchange membrane 414 (here AEM 414) and including an inlet 406a and an outlet 406b, a first compartment 408 located between AEM 414 and a bipolar membrane 416 and including an inlet 408a and an outlet 408b, a second compartment 410 located between bipolar membrane 416 and a second ion exchange membrane 418 (here CEM 418) and including an inlet 410a and an outlet 410b, and an anode compartment 212 located between CEM 418 and anode 402 and including an inlet 412a and an outlet 414b. Device 400 may include any one, or more, or all of the controllers, valves, pH sensors, and/or flowmeters described herein.

Second compartment 410 of a device 400 also includes an electrooxidation cell 450 with one or more sets of electrodes 440 with electrocatalytic surfaces for the decomposition of urea via electrooxidation. Each set of electrodes can include an anode and a cathode. In an embodiment, the electrodes 440 include a cathode and an anode, and the anodes comprise a transition metal and/or mixtures thereof and/or alloys thereof. The transition metal can be selected from the group consisting of cobalt, copper, iron, nickel, platinum, palladium, iridium, ruthenium, and rhodium. In an embodiment, the cathode can include platinum and the anode comprises wherein the anode comprises nickel, nickel oxide, nickel hydroxide or nickel oxide hydroxide (NiOOH). The electrooxidation cell 450 can also include an alkaline polymeric gel.

A power source 442 provides the electrodes 440 with an electrical charge, and a power source 444 can be used to create a potential difference between the anode 402 and cathode 404. Alternatively, power source 442 and power source 444 can be the same power source. The power source 442 provides the electrodes 440 with an electrical charge to activate an electrocatalytic surface of the electrodes. The voltage difference applied across the electrodes (e.g. cathode and anode) can be sufficient to produce nitrogen gas, carbon dioxide gas, and water. The power source 444 provides an electrical charge to split water in bipolar membrane 416 into $H^+$ and $OH^-$.

Bipolar membrane 416 includes a CEM 420 and an AEM 422. Water can be fed into a water compartment 424 between CEM 420 and AEM 422 from a source of water (not shown). When a potential difference (e.g., a potential difference sufficient to split water) is created between the anode 402 and cathode 404, the potential difference causes water to split into positively charged ions (H+) and negatively charged ions (OH−), and the positively and negatively charged ions generated between CEM 420 and AEM 422 flow through CEM 420 and AEM 422 into the first compartment 408 and second compartment 410, respectively. Specifically, positively charged ions (H+) flow through CEM 420 into first compartment 408 as illustrated by arrow 432, while negatively charged ions (OH−) flow through AEM 422 into second compartment 410 as illustrated by arrow 434. AEM 414 prevents the positively charged ions (H+) from flowing out of first compartment 408, while CEM 418 prevents the negatively charged ions (OH−) from flowing out of second compartment 410.

Figure 9:
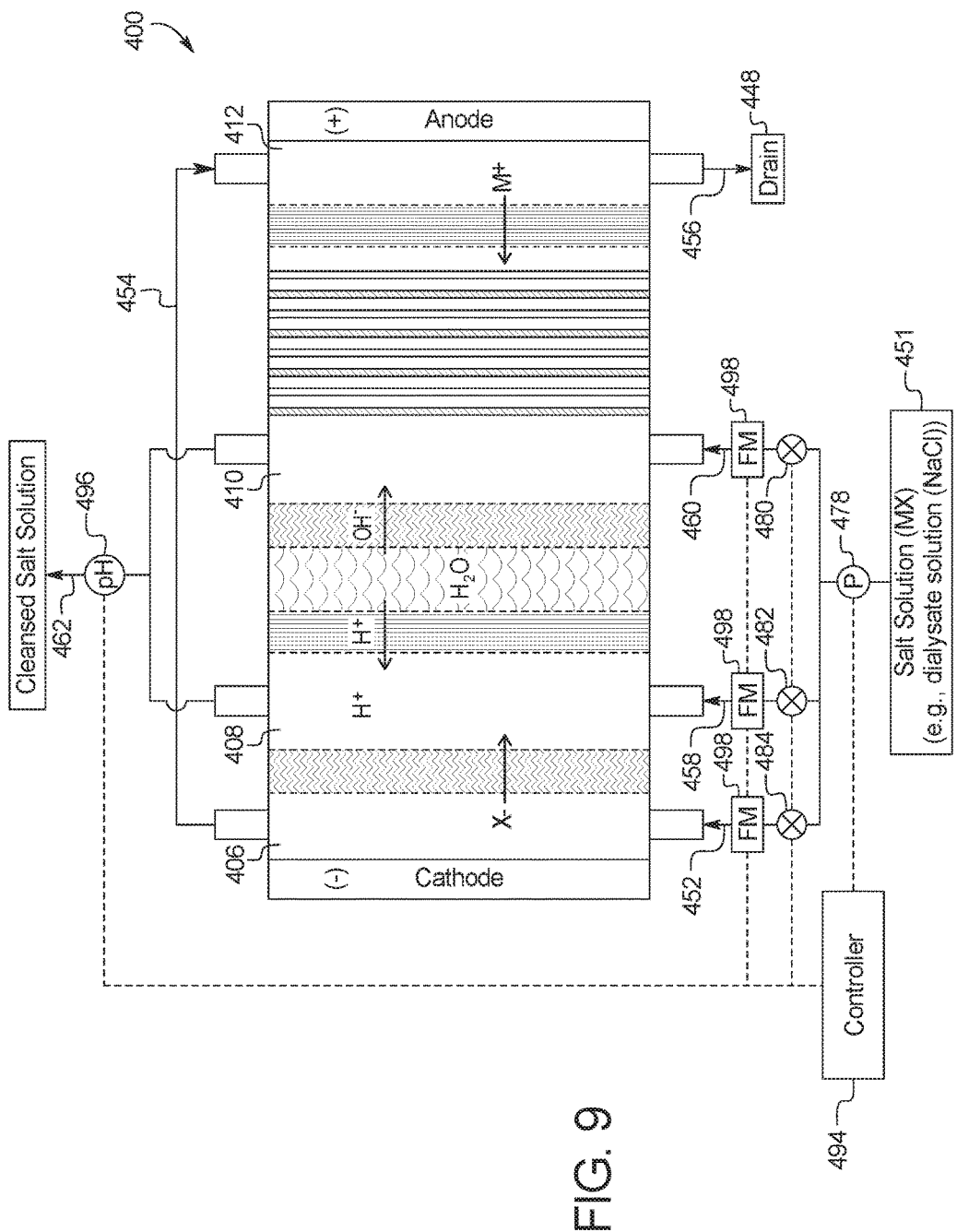
FIG. 9 shows an alternative embodiment of a device for the removal of urea from a fluid having urea to produce a cleansed fluid.

FIG. 9 shows the flow paths of fluid through device 400. As shown by flowpaths 452, 454 and 456, salt solution (MX) from a source 450 can be passed through anode compartment 406 and cathode compartment 412 and sent to drain 448 as described above. The salt solution (MX) can also be passed through each of first compartment 408 (flowpath 458) and second compartment 410 (flowpath 460). As salt solution (MX) passes through first compartment 408, the salt solution becomes more acidic as negatively charged ions (X−) from cathode compartment 406 combine with positively charged ions (H+) from bipolar membrane 416. As salt solution (MX) passes through second compartment 410, the salt solution becomes more basic (alkaline) as positively charged ions (M+) from anode compartment 412 combine with negatively charged ions (OH−) from bipolar membrane 416.

The one or more sets (e.g., [set of electrodes]$_n$, where n can be any integer) of electrodes 440 with electrocatalytic surfaces of electrooxidation cell 450 are located within second compartment 410 because the salt solution (MX) within second compartment 410 becomes more basic (alkaline) as positively charged ions (M+) from anode compartment 412 combine with negatively charged ions (OH−) from bipolar membrane 416. As explained above, it has been determined that a more basic alkaline solution is better for the decomposition of urea via electrooxidation. The urea cleansed salt solution can then be combined with the acidic solution from first compartment 408, as indicated by flowpath 462, to neutralize the overall pH of the combined solution output by device 400.

In use, second compartment 410 can receive much more solution than first compartment 408, so that the majority of salt solution output at flowpath 462 is cleansed of urea via electrooxidation. In an embodiment, the source of salt solution 450 outputs about 405 mL/min of salt solution. 5 mL/min is directed to anode compartment 406 and cathode compartment 412 along flowpaths 452, 454 and 456, 10 mL/min is directed to first compartment 408 along flowpath 458, and the other 390 mL/min is directed to second compartment 410 along flowpath 460. Thus, 96% of the salt solution leaving source 450, and 97.5% of the cleansed solution leaving device 400 at flowpath 462, is cleansed of urea via electrooxidation.

FIG. 9 illustrates that in an embodiment, device 400 may include one or more pump 478, and a plurality of valves 480, 482, 484 that control fluid flow along the respective flowpaths. Pump 478 may be a peristaltic pump or a volume membrane pump. The valves 480, 482, 484 may be variable fluid orifice valves that allow a percentage of fluid to flow through each respective flowpath. Alternatively, the valves can be solenoid valves or other valves known to those of ordinary skill in the art. In the illustrated embodiment, the valves 480, 482, 484 are electrically connected to a controller 494. The controller 494 may include one or more processor and memory programmed to control one or more pump 478 and the variable orifice size of valves 480, 482, 484 to achieve the flow rates and percentages discussed above or to achieve other flowrates and percentages through the respective flowpaths.

In an embodiment, any one or more or all of valves 480, 482, 484 may alternatively be solenoid valves that operate with controller 494 so that they are opened a specified amount of time to achieve the flow distributions through device 400 described above. In a further embodiment, one or more valves, such as valves 480, 482, 484, may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 494 can precisely meter fluid through the flowpaths by toggling the solenoid valves of the balance chamber between the first compartment and the second compartment and control flow rate by controlling how often the inlet and outlet valves are cycled.

In an embodiment, device 400 includes a pH sensor 496 that ensures the pH of the cleansed salt solution is at or near 7.0 (i.e., neutral). The pH sensor 496 may provide feedback to controller 494, so that controller 494 controls pump 478 and/or valves 480, 482, 484 to raise or lower the pH of the outflow as necessary. Device 400 may also include one or more flowmeters (FM) 498 to monitor flow at any desired one or more location within the respective flowpaths of device 400 and provide flowrate feedback to controller 494.

Figure 10:
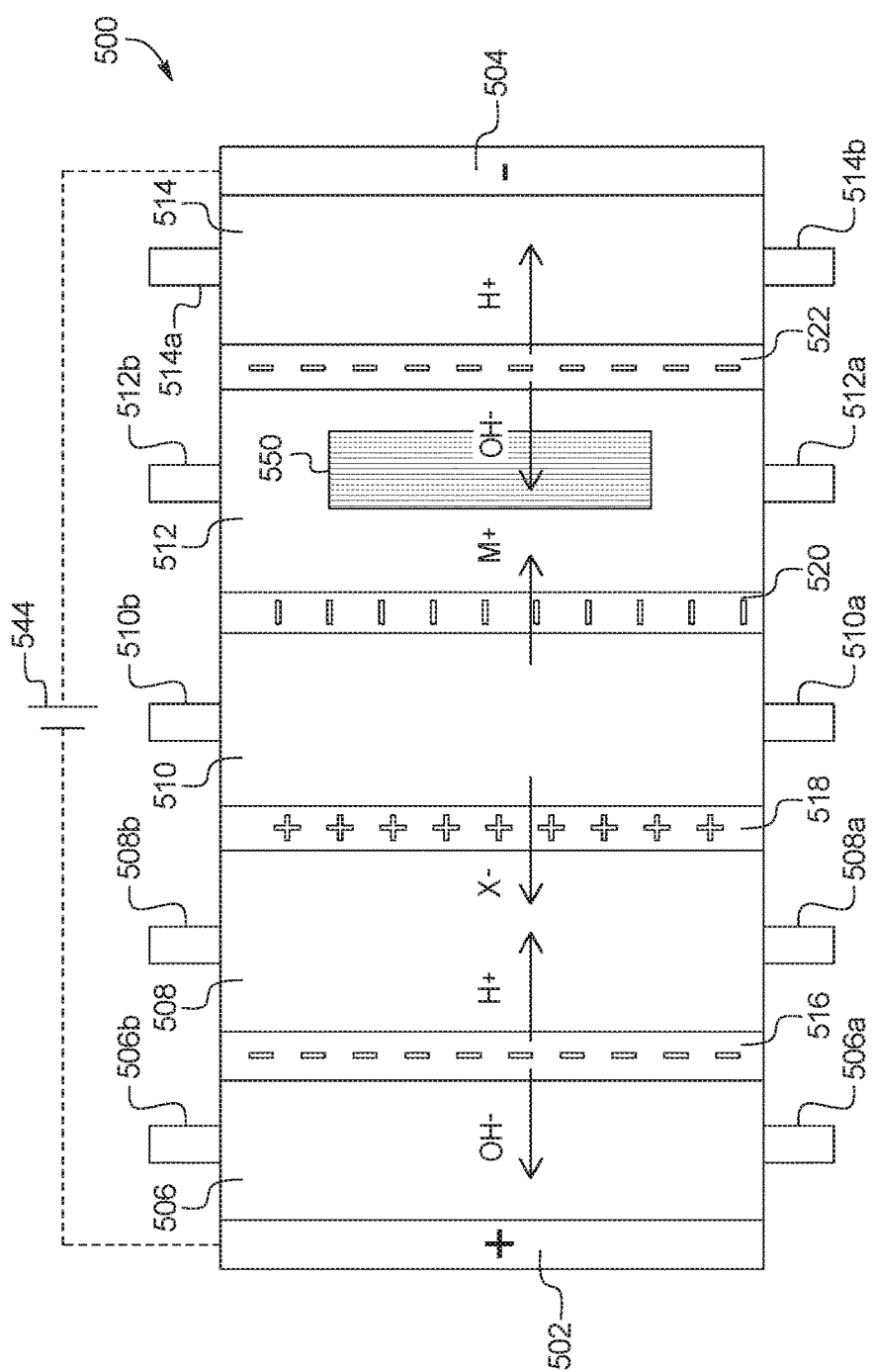
FIG. 10 shows an alternative embodiment of a device for the removal of urea from a fluid having urea to produce a cleansed fluid.

FIG. 10 illustrates a device 500 that combines the urea decomposition and electrodialysis units discussed above into the same unit. More specifically, device 500 takes the electrodes from urea decomposition unit 50 and places the electrodes inside of one or more compartment of electrodialysis unit 200. The oxidation of urea from salt solution therefore occurs inside of the compartment due to the electrocatalytic surfaces of the electrodes for decomposition of urea via electrooxidation. Device 500 may be used with any of the controllers, valves, pH sensors, and/or flowmeters described herein.

Similar to above, device 500 is a three-compartment electrodialysis unit including an anode 502 and a cathode 504 for separation of a salt solution via electrodialysis. Device 500 includes an anode compartment 506 located between anode 502 and a bipolar membrane 516 and including an inlet 506*a* and an outlet 506*b*, a first compartment 508 located between bipolar membrane 516 and a first ion exchange membrane 518 (here AEM 518) and including an inlet 508*a* and an outlet 508*b*, a second compartment 510 located between AEM 518 and a second ion exchange membrane 520 (here CEM 520) and including an inlet 510*a* and an outlet 510*b*, a third compartment 512 located between CEM 520 and a bipolar membrane 522 and including an inlet 512*a* and an outlet 512*b*, and a cathode compartment 514 located between bipolar membrane 522 and cathode 504 and including an inlet 514*a* and an outlet 514*b*. In a further embodiment, an electrodialysis unit may comprise repeats of the above-described three-compartment electrodialysis unit (i.e., [three-compartment electrodialysis unit]$_n$, where n can be any integer).

Third compartment 512 of device 5000 also includes an electrooxidation cell 550 with one or more sets of electrodes with electrocatalytic surfaces for the decomposition of urea via electrooxidation. As discussed above, each set of electrodes can include an anode and a cathode. In an embodiment, the electrodes include a cathode and an anode, and the anodes comprise a transition metal and/or mixtures thereof and/or alloys thereof. The transition metal can be selected from the group consisting of cobalt, copper, iron, nickel, platinum, palladium, iridium, ruthenium, and rhodium. In an embodiment, the cathode can include platinum and the anode comprises wherein the anode comprises nickel, nickel oxide, nickel hydroxide or nickel oxide hydroxide (NiOOH). The urea electrooxidation cell 550 can also include an alkaline polymeric gel.

A power source (not shown) provides the electrodes of electrooxidation cell 550 with an electrical charge, and a power source 544 can be used to create a potential difference between the anode 502 and cathode 504. Alternatively, the same power source can be used for electrooxidation cell 550 and to create a potential difference between the anode 502 and cathode 504. The power source (not shown) provides the electrodes of electrooxidation cell 550 with an electrical charge to activate an electrocatalytic surface of the electrodes. The voltage difference applied across the electrodes (e.g. cathode and anode) can be sufficient to produce nitrogen gas, carbon dioxide gas, and water. The power source 444 provides an electrical charge to split water in bipolar membranes 516 and 522 into $H^+$ and $OH^-$.

Bipolar membranes 516 and 522 each include a CEM and an AEM as described above with respect to bipolar membrane 112. For each bipolar membrane 516 and 522, water can be fed into a water compartment between the CEM and AEM from a source of water. For simplicity, the water compartment, CEM and AEM are not shown separately in FIG. 10. When a potential difference (e.g., a potential difference sufficient to split water) is created between the anode 502 and cathode 504, the potential difference causes water to split into positively charged ions (H+) and negatively charged ions (OH−) in bipolar membranes 516 and 522. The generated negatively charged ions (OH−) from bipolar membrane 516 flow through the AEM and into cathode compartment 506, and the generated positively charged ions (H+) flow through the CEM and into first compartment 508. Similarly, the potential difference causes the negatively charged ions (OH−) generated in the bipolar membrane 522 to flow through the AEM and into third compartment 512, and the positively charged ions (H+) to flow through the CEM and into cathode compartment 514.

Figure 11:
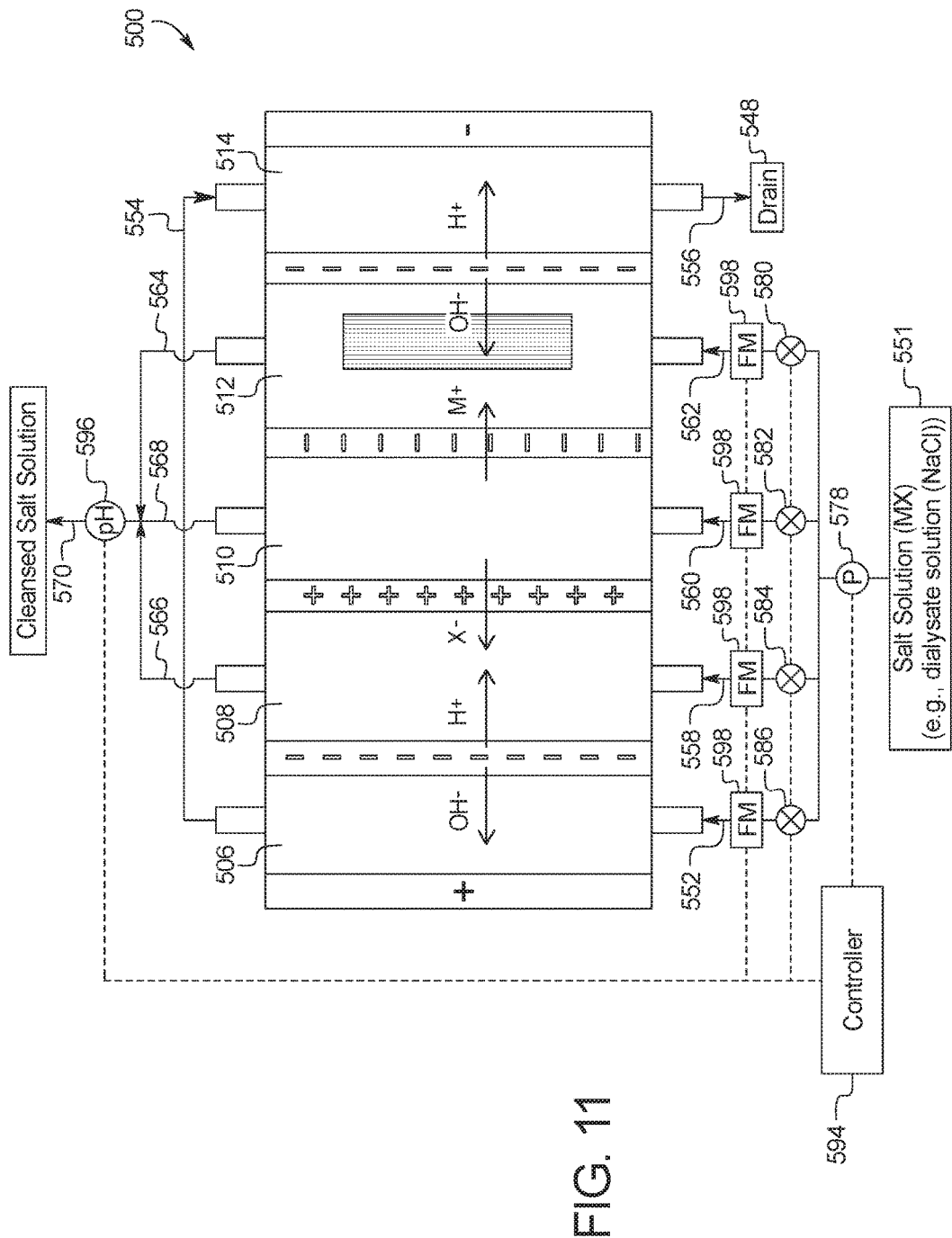
FIG. 11 shows an alternative embodiment of a device for the removal of urea from a fluid having urea to produce a cleansed fluid.

FIG. 11 shows the flow paths of fluid through device 500. As shown by flowpaths 552, 554 and 556, salt solution (MX) from a source 551 can be passed through anode compartment 506 and cathode compartment 514 and sent to drain 548 as described above. The salt solution can also be passed through each of first compartment 508 (flowpath 558), second compartment 510 (flowpath 560) and third compartment 512 (flowpath 562). As salt solution passes through second compartment 510, the potential difference created between the anode 202 and cathode 204 drives negatively charged ions (X−) through AEM 518 and into first compartment 508. Likewise, the potential difference created between the anode 502 and cathode 504 drives positively charged ions (M+) through CEM 520 and into third compartment 512. The CEM of bipolar membrane 516 prevents the negatively charged ions (X−) from flowing out of first compartment 508, while the AEM of bipolar membrane 522 prevents the positively charged ions (M+) from flowing out of third compartment 512. The potential difference created between anode 502 and cathode 504 therefore causes positively charged ions (H+) and negatively charged ions (X−) in first compartment 508 to create an acidic solution (HX) with a low pH. Similarly, the potential difference created between anode 502 and cathode 504 causes negatively charged ions (OH−) and positively charged ions (M+) in third compartment 512 to create a basic solution (MOH) with a high pH.

The one or more sets (e.g., [set of electrodes]$_n$, where n can be any integer) of electrodes with electrocatalytic surfaces of electrooxidation cell 550 are located within third compartment 512 because the salt solution (MX) within third compartment 512 becomes more basic (alkaline) as positively charged ions (M+) from second compartment 510 combine with negatively charged ions (OH−) from bipolar membrane 522. As explained above, it has been determined that a more basic alkaline solution is better for the decomposition of urea via electrooxidation. The urea cleansed salt solution from flowpath 564 can then be combined with the acidic solution from first compartment 508 and solution from second compartment 510, as indicated by flowpaths 566 and 568, respectively, to neutralize the overall pH of the combined solution output by device 500.

In use, third compartment 512 can receive much more solution than first compartment 508 and second compartment 510, so that the majority of salt solution output at flowpath 570 is cleansed of urea via electrooxidation. In an embodiment, the source of salt solution 551 outputs about 405 mL/min of salt solution. 5 mL/min is directed to anode compartment 506 and cathode compartment 512 along flowpaths 552, 554 and 556, 10 mL/min is directed to first compartment 508 along flowpath 558, 10 mL/min is directed to second compartment 510 along flowpath 560, and the other 380 mL/min is directed to third compartment 512 along flowpath 562. Thus, 94% of the salt solution leaving source 551, and 95% of the cleansed solution leaving device 500 at flowpath 570, is cleansed of urea via electrooxidation.

FIG. 11 illustrates that in an embodiment, device 500 may include one or more pump 578, and a plurality of valves 580, 582, 584, 586 that control fluid flow along the respective flowpaths. Pump 578 may be a peristaltic pump or a volume membrane pump. The valves 580, 582, 584, 586 may be variable fluid orifice valves that allow a percentage of fluid to flow through each respective flowpath. Alternatively, the valves can be solenoid valves or other valves known to those of ordinary skill in the art. In the illustrated embodiment, the valves 580, 582, 584, 586 are electrically connected to a controller 594. The controller 594 may include one or more processor and memory programmed to control one or more pump 578 and the variable orifice size of valves 580, 582, 584, 586 to achieve the flow rates and percentages discussed above or to achieve other flowrates and percentages through the respective flowpaths.

In an embodiment, any one or more or all of valves 580, 582, 584, 586 may alternatively be solenoid valves that operate with controller 594 so that they are opened a specified amount of time to achieve the flow distributions through device 500 described above. In a further embodiment, one or more valves, such as valves 580, 582, 584, 586, may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 594 can precisely meter fluid through the flowpaths by toggling the solenoid valves of the balance chamber between the first compartment and the second compartment and control flow rate by controlling how often the inlet and outlet valves are cycled.

In an embodiment, device 500 includes a pH sensor 596 that ensures the pH of the cleansed salt solution is at or near 7.0 (i.e., neutral). The pH sensor 596 may provide feedback to controller 594, so that controller 594 controls pump 578 and/or valves 580, 582, 584, 586 to raise or lower the pH of the outflow as necessary. Device 500 may also include one or more flowmeters (FM) 598 to monitor flow at any desired one or more location within the respective flowpaths of device 500 and provide flowrate feedback to controller 594.

Figure 12:
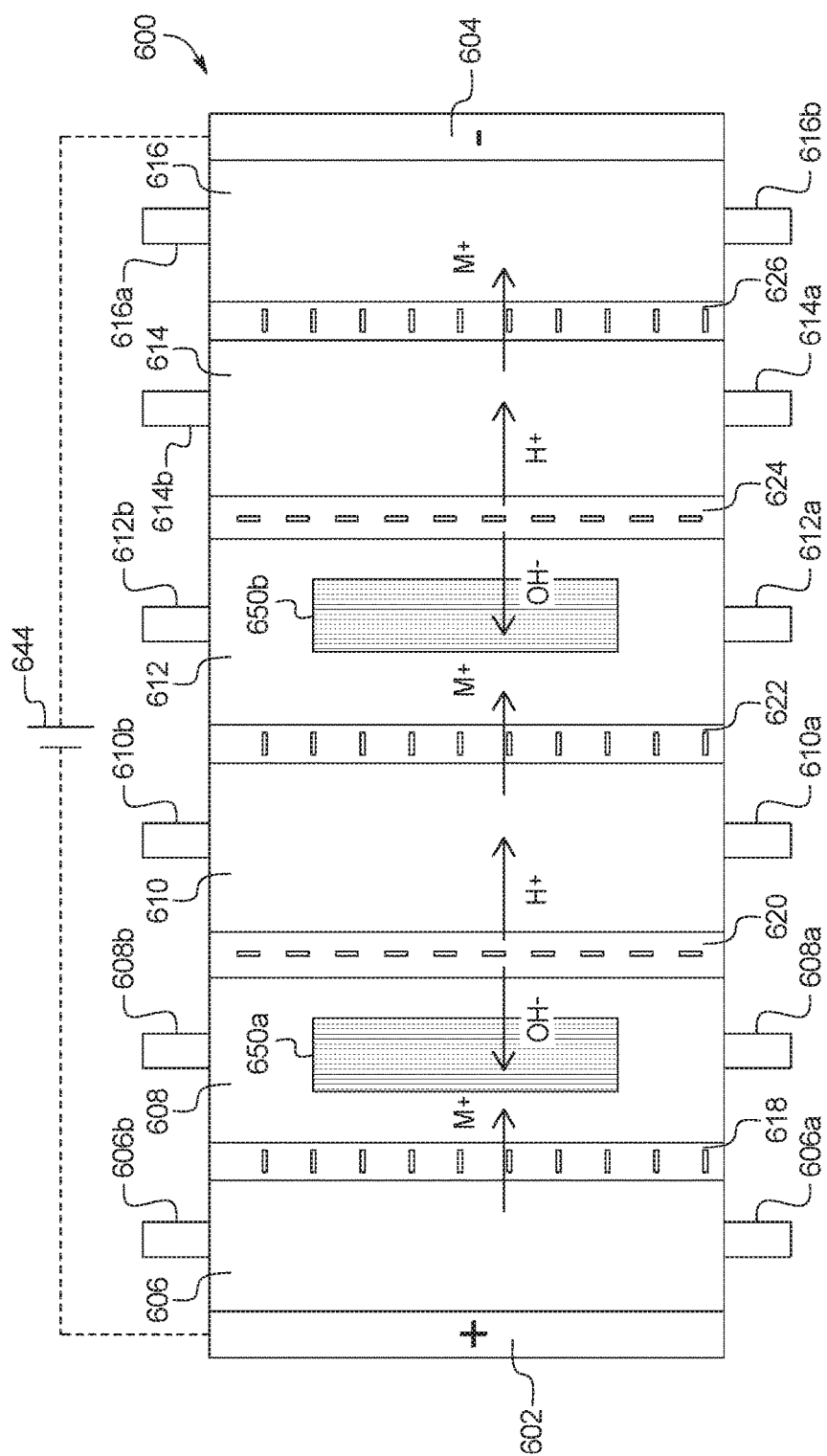
FIG. 12 shows an alternative embodiment of a device for the removal of urea from a fluid having urea to produce a cleansed fluid.

FIG. 12 illustrates a device 600 that combines the urea decomposition and electrodialysis units discussed above into the same unit. More specifically, device 600 takes the electrodes from urea decomposition unit 50 and places the electrodes inside of multiple compartments of electrodialysis unit 300. The oxidation of urea from salt solution therefore occurs inside of the compartment due to the electrocatalytic surfaces of the electrodes for decomposition of urea via electrooxidation. Device 600 may be used with any one, or more, or all of the controllers, valves, pH sensors, and/or flowmeters described herein.

Similar to above, device 600 is a two-compartment, two-cell electrodialysis unit including an anode 602 and a cathode 604 for separation of a salt solution via electrodialysis. Device 600 includes an anode compartment 606 located between anode 602 and a first ion exchange membrane 618 and including an inlet 606a and an outlet 606b, a first compartment 608 located between first ion exchange membrane 618 and a bipolar membrane 620 and including an inlet 608a and an outlet 608b, a second compartment 610 located between bipolar membrane 620 and a second ion exchange membrane 622 and including an inlet 610a and an outlet 610b, a third compartment 612 located between second ion exchange membrane 622 and a bipolar membrane 624 and including an inlet 612a and an outlet 612b, a fourth compartment 614 located between bipolar membrane 624 and a third ion exchange membrane 626 and including an inlet 614a and an outlet 614b, and a cathode compartment 616 located between third ion exchange membrane 626 and cathode 604 and including an inlet 616a and an outlet 616b. In the illustrated embodiment, the first ion exchange membrane 618, second ion exchange membrane 622 and third ion exchange membrane 626 are each a CEM.

First compartment 608 and third compartment 612 of device 600 each include an electrooxidation cell 650a, 650b with one or more sets of electrodes with electrocatalytic surfaces for the decomposition of urea via electrooxidation. As described above, each set of electrodes can include an anode and a cathode. In an embodiment, the electrodes include a cathode and an anode, and the anodes comprise a transition metal and/or mixtures thereof and/or alloys thereof. The transition metal can be selected from the group consisting of cobalt, copper, iron, nickel, platinum, palladium, iridium, ruthenium, and rhodium. In an embodiment, the cathode can include platinum and the anode comprises wherein the anode comprises nickel, nickel oxide, nickel hydroxide or nickel oxide hydroxide (NiOOH). The electrooxidation cell 650a, 650b can also include an alkaline polymeric gel.

A power source (not shown) provides the electrodes of electrooxidation cells 650a, 650b with an electrical charge, and a power source 644 can be used to create a potential difference between the anode 602 and cathode 604. Alternatively, the same power source can be used for electrooxidation cells 650a, 650b and to create a potential difference between the anode 602 and cathode 604. The power source (not shown) provides the electrodes of electrooxidation cells 650a, 650b with an electrical charge to activate an electrocatalytic surface of the electrodes. The voltage difference applied across the electrodes (e.g. cathode and anode) can be sufficient to produce nitrogen gas, carbon dioxide gas, and water. The power source 644 provides an electrical charge to split water in bipolar membranes 620 and 624 into H+ and OH−.

Bipolar membranes 620 and 624 each include a CEM and an AEM as described above with respect to bipolar membrane 112. For each bipolar membrane 620 and 624, water can be fed into a water compartment between the CEM and AEM from a source of water. For simplicity, the water compartment, CEM and AEM are not shown separately in FIG. 12. When a potential difference (e.g., a potential difference sufficient to split water) is created between the anode 602 and cathode 604, the potential difference causes water to split into positively charged ions (H+) and negatively charged ions (OH−). The generated negatively charged ions (OH−) from bipolar membrane 620 flow through the AEM and into first compartment 608, and the generated positively charged ions (H+) flow through the CEM and into second compartment 610. Similarly, the potential difference causes the negatively charged ions (OH−) from bipolar membrane 624 to flow through the AEM and into third compartment 612, and causes the positively charged ions (H+) to flow through the CEM and into fourth compartment 614.

Figure 13:
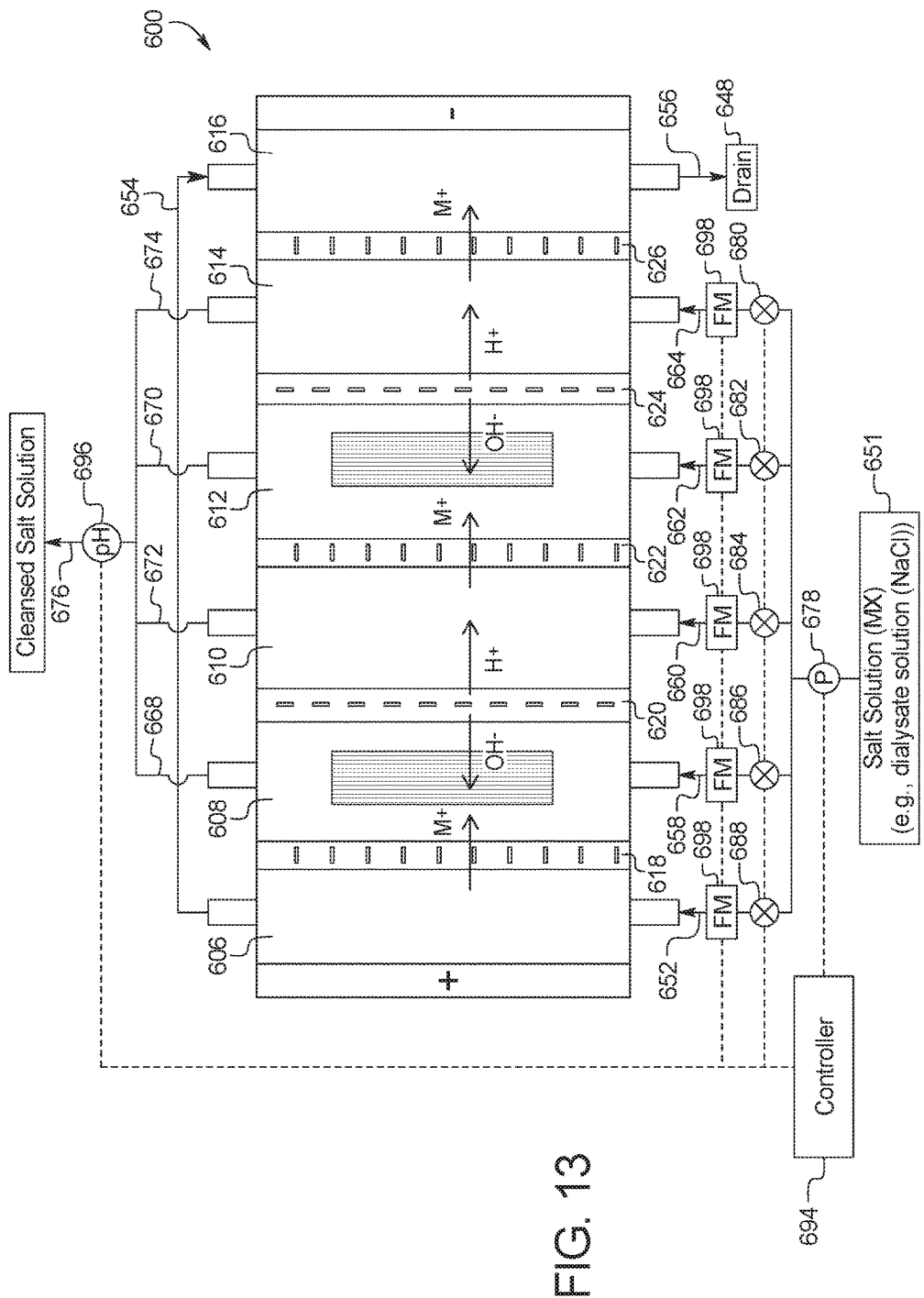
FIG. 13 shows an alternative embodiment of a device for the removal of urea from a fluid having urea to produce a cleansed fluid.

FIG. 13 shows the flow paths of fluid through device 600. As shown by flowpaths 652, 654 and 656, salt solution (MX) from a source 651 can be passed through anode compartment 606 and cathode compartment 616 and sent to drain 648 as described above. A salt solution can also be passed through each of first compartment 608 (flowpath 658), second compartment 610 (flowpath 660), third compartment 612 (flowpath 662) and fourth compartment 614 (flowpath 664). In the illustrated embodiment, first ion exchange membrane 618 is a first CEM 618, second ion exchange membrane 622 is a second CEM 622, and third ion exchange membrane 626 is a third CEM 626. Salt solution (MX) passing through anode compartment 606 therefore loses positively charged ions (M+) through CEM 618 to first compartment 608, salt solution passing through second compartment 610 loses positively charged ions (M+) through CEM 622 to third compartment 612, and salt solution passing through fourth compartment 614 loses positively charged ions (M+) through CEM 326 to cathode compartment 616. The AEM of bipolar membrane 620 prevents the positively charged ions (M+) from flowing out of first compartment 608, while the AEM of bipolar membrane 624 prevents the positively charged ions (M+) from flowing out of third compartment 612. The potential difference created between anode 602 and cathode 604 causes negatively charged ions (OH−) and positively charged ions (M+) to form a basic solution (MOH) with a high pH in first compartment 608 and third compartment 612.

The one or more sets (e.g., [set of electrodes]$_n$, where n can be any integer) of electrodes with electrocatalytic surfaces of electrooxidation cell 650a are located within first compartment 608 because the salt solution (MX) within first compartment 608 becomes more basic (alkaline) as positively charged ions (M+) from anode compartment 606 combine with negatively charged ions (OH−) from bipolar membrane 620. The one or more sets (e.g., [set of electrodes]$_n$, where n can be any integer) of electrodes with electrocatalytic surfaces of electrooxidation cell 650b are located within third compartment 612 because the salt solution (MX) within third compartment 612 becomes more basic (alkaline) as positively charged ions (M+) from second compartment 610 combine with negatively charged ions (OH−) from bipolar membrane 624. As explained above, it has been determined that a more basic alkaline solution is better for the decomposition of urea via electrooxidation. The urea cleansed salt solution from flowpaths 668 and 670 can then be combined with the acidic solution from second compartment 610 and fourth compartment 614, as indicated by flowpaths 672 and 674, respectively, to neutralize the overall pH of the combined solution output by device 600 at flowpath 676.

In use, first compartment 608 and third compartment 612 can receive much more solution than second compartment 610 and fourth compartment 614, so that the majority of salt solution output at flowpath 676 is cleansed of urea via electrooxidation. In an embodiment, the source of salt solution 651 outputs about 405 mL/min of salt solution. 5 mL/min is directed to anode compartment 606 and cathode compartment 616 along flowpaths 652, 654 and 656, 10 mL/min is directed to second compartment 610 along flowpath 660, 10 mL/min is directed to fourth compartment 614 along flowpath 664, and the other 380 mL/min is split between first compartment 608 and third compartment 612 along flowpaths 658 and 662, respectively (e.g., 190 mL/min along flowpath 658 and 190 mL/min along flowpath 662). Thus, 94% of the salt solution leaving source 651, and 95% of the cleansed solution leaving device 600 at flowpath 676, is cleansed of urea via electrooxidation.

FIG. 13 illustrates that in an embodiment, device 600 may include one or more pump 678, and a plurality of valves 680, 682, 684, 686, 688 that control fluid flow along the respective flowpaths. Pump 678 may be a peristaltic pump or a volume membrane pump. The valves 680, 682, 684, 686, 688 may be variable fluid orifice valves that allow a percentage of fluid to flow through each respective flowpath. Alternatively, the valves can be solenoid valves or other valves known to those of ordinary skill in the art. In the illustrated embodiment, the valves 680, 682, 684, 686, 688 are electrically connected to a controller 694. The controller 694 may include one or more processor and memory programmed to control one or more pump 678 and the variable orifice size of valves 680, 682, 684, 686, 688 to achieve the flow rates and percentages discussed above or to achieve other flowrates and percentages through the respective flowpaths.

In an embodiment, any one or more or all of valves 680, 682, 684, 686, 688 may alternatively be solenoid valves that operate with controller 694 so that they are opened a specified amount of time to achieve the flow distributions through device 500 described above. In a further embodiment, one or more valves, such as valves 680, 682, 684, 686, 688, may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, controller 494 can precisely meter fluid through the flowpaths by toggling the solenoid valves of the balance chamber between the first compartment and the second compartment and control flow rate by controlling how often the inlet and outlet valves are cycled.

In an embodiment, device 600 includes a pH sensor 696 that ensures the pH of the cleansed salt solution is at or near 7.0 (i.e., neutral). The pH sensor 696 may provide feedback to controller 694, so that controller 694 controls pump 678 and/or valves 680, 682, 684, 686, 688 to raise or lower the pH of the outflow as necessary. Device 600 may also include one or more flowmeters (FM) 698 to monitor flow at any desired one or more location within the respective flowpaths of device 600 and provide flowrate feedback to controller 694.

Figure 14:
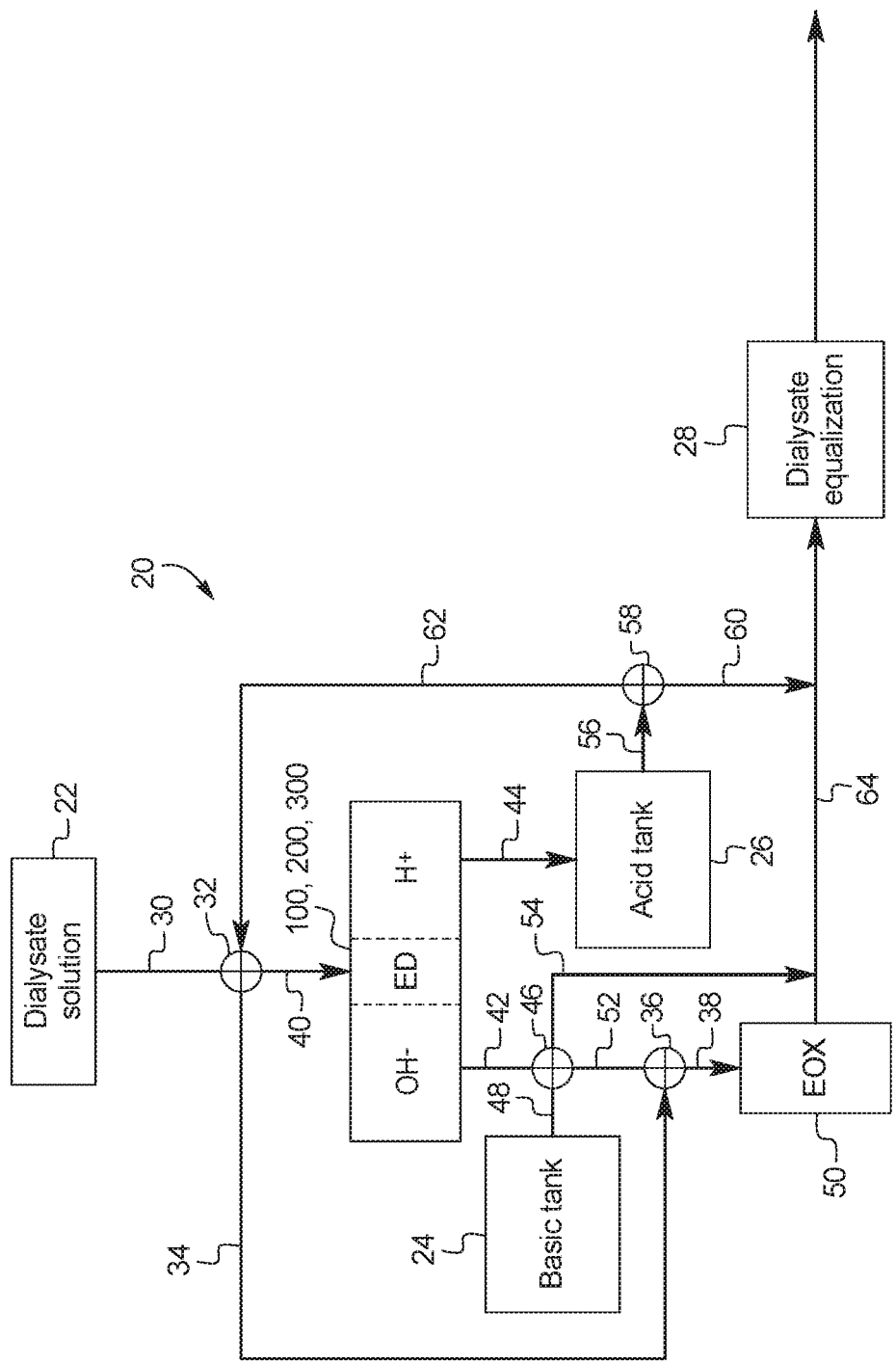
FIG. 14 shows an alternative embodiment of a device for the removal of urea from a fluid having urea to produce a cleansed fluid.

FIG. 14 illustrates an embodiment of a device 20 for the removal of urea from a fluid having urea to produce a cleansed fluid. In the illustrated embodiment, device 20 includes a urea decomposition unit 50 and an electrodialysis unit 100, 200, 300 as described above. Device 20 further includes a source of dialysis solution 22, a basic tank 24, an acid tank 26 and a dialysis fluid equalization unit 28. Device 20 may also employ any one or more of the controllers, one or more pump, valves, pH sensors, and/or flowmeters described herein.

In the illustrated embodiment, salt solution containing urea first passes from the source of dialysis fluid solution 22 to either of (i) urea decomposition unit 50 to be oxidized or (ii) electrodialysis unit 100, 200, 300 to be separated into an acidic solution and a basic solution. As illustrated, dialysis fluid solution first passes to valve 32 via flowpath 30. Valve 32 can then direct the dialysis solution to urea decomposition unit 50 via flowpath 34, valve 36 and flowpath 38, or valve 32 can direct the dialysis solution to electrodialysis unit 100, 200, 300 via flowpath 40.

Electrodialysis unit 100, 200, 300 separates the dialysis fluid solution into a basic solution and an acid solution as described above. The basic solution flows out of electrodialysis unit 100, 200, 300 at flowpath 42. The acidic solution flows out of electrodialysis unit 100, 200, 300 at flowpath 44.

Valve 46 can either (i) direct the basic solution to flowpath 48 to be stored in basic tank 24, (i) direct the basic solution to flowpaths 52 and 38 to be mixed with original dialysis fluid from source 22 before the original dialysis fluid is directed to urea decomposition unit 50, or (iii) direct the basic solution to flowpath 54 to mix with dialysis fluid solution that has exited urea decomposition unit 50. Valve 46 can therefore be used to precisely control the pH of fluid entering or leaving urea decomposition unit 50. If the solution entering or leaving urea decomposition unit 50 needs the pH raised more than what can be provided by the basic solution flowing out of flowpath 42, valve 46 allows additional basic solution to be pulled from basic solution tank 24 along flowpath 48.

Acid tank 26 receives acidic solution from electrodialysis unit 100, 200, 300. The acidic solution can then be flowed to valve 58 via flowpath 56. Valve 58 can either (i) direct the acidic solution via flowpath 60 to be mixed with oxidized solution leaving urea decomposition unit 50 to lower the pH of the oxidized solution leaving urea decomposition unit 50, or (ii) direct the acidic solution back to valve 32 via flowpath 62, so that the acidic solution can then be directed through one or more of the flowpaths and components of device 20 after treatment to clean the flowpaths and components. It should be understood from FIG. 10 that the acidic solution can be directed through any of the valves and flowpaths and any of urea decomposition unit 50, electrodialysis unit 100, 200, 300, basic tank 24, acid tank 26 and dialysis fluid equalization unit 28, in order to clean these valves, flowpaths and other components.

Dialysis fluid equalization unit 28 can be used to neutralize the dialysis fluid that has been cleaned of urea by urea decomposition unit 50. In an embodiment, the pH of dialysis fluid exiting urea decomposition unit 50 is measured at dialysis fluid equalization unit 28. If the measured pH is too high, dialysis fluid equalization unit 28 receives additional acidic solution from acid tank 26, via flowpaths 56, 60 and 64, so that the pH can be lowered to an acceptable level. If the measured pH is too low, dialysis fluid equalization unit 28 receives additional basic solution from basic tank 24, via flowpaths 48, 54 and 64, so that the pH can be raised to an acceptable level. Dialysis fluid equalization unit 28 can continue to measure the pH of the dialysis fluid solution therein and receive acidic and basic solution until the dialysis fluid solution therein is safe for treatment. In an alternative embodiment, the pH of solution leaving urea decomposition unit 50 can be balanced and immediately used for renal failure therapy.

The methods of the present disclosure preferably remove a substantial amount of urea from a solution containing urea including, for example, 10%, 20%, 30%, 40%, 50%, 60%, 70%, 80%, 90%, or 100% of the urea.

During operation of the disclosed devices, $Ca^{2+}$ and $Mg^{2+}$ may be depleted in urea decomposition unit 50 and electrodialysis unit 100, 200, 300. Without wishing to be bound by a theory of the invention, it is believed that $Ca^{2+}$ and $Mg^{2+}$ become depleted during operation of the disclosed devices due to hydroxide formation and precipitation. To remove calcium and magnesium precipitates, the acidic solution stored in the acid tank is circulated through the urea decomposition unit 50 and electrodialysis unit 100, 200, 300. The acid solution solubilizes the calcium and magnesium precipitates and thus prevents membrane and electrode fouling while restoring $Ca^{2+}$ and $Mg^{2+}$ to the cleansed salt solution. In an embodiment, the devices disclosed herein can include a central controller than controls all of the pumps and valves, as well as the flowrates through the flowpaths. It should be understood that the arrows shown in the figures herein represent flowpaths, and that one or more pumps can be included along any of the flowpaths disclosed herein to pump fluid through the flowpaths. Valves can also be positioned anywhere along any of the flowpaths for the same purpose. By controlling the pumps and valves, central controller can control the flowrates through the flowpaths and the pH of the anywhere in the system. It should be understood from the present disclosure that any of the devices described above can be included in a dialysis fluid circuit of a renal replacement therapy system. In an embodiment, the sources of salt solution discussed above can be sources of used/used dialysis fluid from the renal replacement therapy system. In an embodiment, the cleansed salt solution illustrated in the Figures herein can be regenerated dialysis fluid that can be reused by the renal replacement therapy system for treatment of a patient. The salt solution discussed herein can be any type of dialysis fluid/renal therapy solution containing urea. In an embodiment, the renal replacement therapy system can be a hemodialysis system, a peritoneal dialysis system, a hemofiltration system or a hemodiafiltration system.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A device for the removal of urea from a fluid having urea to produce a cleansed fluid, the device comprising:
   a urea decomposition unit comprising an inlet for entry of the fluid having urea and an outlet for removal of the cleansed fluid, and one or more sets of electrodes each having an anode and a cathode, wherein the anode of the one or more sets of electrodes is provided with an electrocatalytic surface for decomposition of urea via electrooxidation; and
   an electrodialysis unit comprising
      a bipolar membrane;
      at least two ion exchange membranes; and
      a set of electrodes having an anode and a cathode for separation of the fluid having urea via electrodialysis, where the fluid having urea is separated into an acid stream and a basic stream,
   wherein the basic stream of the electrodialysis unit is placed in fluid communication with the inlet of the urea decomposition unit, wherein the basic stream of the electrodialysis unit is oxidized by the one or more set of electrodes, and wherein the acid stream separated from the fluid having urea is placed in fluid communication with the basic stream oxidized by the one or more set of electrodes of the urea decomposition unit to produce a neutralized, cleansed fluid.

2. The device of claim 1, wherein the electrodialysis unit comprises a first cell comprising the bipolar membrane, a first ion exchange membrane, and a second ion exchange membrane, wherein the first ion exchange membrane is positioned next to one side of the bipolar membrane and the second ion exchange membrane is positioned next to an opposite side of the bipolar membrane, thereby forming (i) a first compartment between the bipolar membrane and the first ion exchange membrane and (ii) a second compartment between the bipolar membrane and the second ion exchange membrane.

3. The device of claim 2, wherein the first ion exchange membrane is an anion exchange membrane or a cation exchange membrane.

4. The device of claim 2, wherein the second ion exchange membrane is an anion exchange membrane or a cation exchange membrane.

5. The device of claim 2, wherein the bipolar membrane is a first bipolar membrane, wherein the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

6. The device of claim 5, wherein each of the first, second, and third ion exchange membranes are cation exchange membranes, or wherein each of the first, second, and third ion exchange membranes are anion exchange membranes.

7. The device of claim 1, wherein the bipolar membrane is a first bipolar membrane, wherein the electrodialysis unit comprises a cell including the first bipolar membrane, a second bipolar membrane, a first ion exchange membrane, and a second ion exchange membrane, and wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

8. The device of claim 7, wherein the first ion exchange membrane is a cation exchange membrane and the second ion exchange membrane is an anion exchange membrane.

9. The device of claim 1, wherein a power source in the urea decomposition unit provides the electrodes with an electrical charge to activate the electrocatalytic surface of the electrodes.

10. The device of claim 1, wherein a power source in the electrodialysis unit provides the electrodes with an electrical charge to split water in the bipolar membrane into $H^+$ and $OH^-$.

11. The device of claim 1, wherein the electrodialysis unit separates the fluid having urea via bipolar membrane electrodialysis.

12. The device of claim 1, wherein the fluid having urea is a dialysis fluid.

13. The device of claim 12, wherein the dialysis fluid includes one or more substance selected from the group consisting of: a sodium salt, a magnesium salt, a calcium salt, lactate, carbonate, acetate, citrate, and phosphate.

14. The device of claim 1 further comprising a tank for the fluid having urea.

15. The device of claim 1, wherein the basic stream includes NaOH.

16. The device of claim 1, wherein the acid stream includes HCl.

17. The device of claim 1, wherein the electrocatalytic surface for decomposition of urea comprises a transition metal and/or mixtures thereof and/or alloys thereof.

18. The device of claim 17, wherein the transition metal is cobalt, copper, iron, nickel, platinum, palladium, iridium, ruthenium, or rhodium.

19. The device of claim 17, wherein the anode in the urea decomposition unit comprises nickel, nickel oxide, nickel hydroxide or nickel oxide hydroxide (NiOOH).

20. The device of claim 1, wherein the urea decomposition unit includes an alkaline polymeric gel.

21. The device of claim 1, wherein the fluid having urea is a dialysis fluid contaminated with urea.

22. The device of claim 1, wherein a voltage difference applied across the cathode and the anode in the urea decomposition unit is sufficient to produce nitrogen gas, carbon dioxide gas, and water.

23. A renal replacement therapy system comprising:
a dialysis fluid circuit, wherein the dialysis fluid circuit comprises a device for the removal of urea from a dialysis fluid having urea to produce a cleansed dialysis fluid, the device comprising:
a urea decomposition unit comprising an inlet for entry of the dialysis fluid having urea and an outlet for removal of the cleansed dialysis fluid, and a set of electrodes having an anode and a cathode, wherein the anode of the set of electrodes is provided with an electrocatalytic surface for decomposition of urea via electrooxidation; and
an electrodialysis unit comprising
a bipolar membrane;
at least two ion exchange membranes; and
a set of electrodes having an anode and a cathode for separation of the dialysis fluid having urea via electrodialysis, where the dialysis fluid having urea is separated into an acid stream and a basic stream,
wherein the basic stream of the electrodialysis unit is placed in fluid communication with the inlet of the urea decomposition unit, wherein the basic stream of the electrodialysis unit is oxidized by the one or more set of electrodes, and wherein the acid stream separated from the dialysis fluid having urea is placed in fluid communication with the basic stream oxidized by the set of electrodes of the urea decomposition unit to produce a neutralized, cleansed fluid.

24. The renal replacement therapy system of claim 23, wherein the cleansed dialysis fluid recirculates through the dialysis fluid circuit.

25. The renal replacement therapy system of claim 23, wherein the electrodialysis unit comprises a first cell including the bipolar membrane, a first ion exchange membrane, and a second ion exchange membrane, wherein the first ion exchange membrane is positioned next to one side of the bipolar membrane and the second ion exchange membrane is positioned next to an opposite side of the bipolar membrane, thereby forming a first compartment between the bipolar membrane and the first ion exchange membrane and a second compartment between the bipolar membrane and the second ion exchange membrane.

26. The renal replacement therapy system of claim 25, wherein the first ion exchange membrane is an anion exchange membrane or a cation exchange membrane.

27. The renal replacement therapy system of claim 25, wherein the second ion exchange membrane is an anion exchange membrane or a cation exchange membrane.

28. The renal replacement therapy system of claim 25, wherein the bipolar membrane is a first bipolar membrane, wherein the electrodialysis unit further comprises a second cell including a second bipolar membrane and a third ion exchange membrane, wherein the second cell is positioned next to the first cell, and wherein the second bipolar membrane is positioned between the second ion exchange membrane of the first cell and the third ion exchange membrane, thereby forming a third compartment between the second bipolar membrane and the third ion exchange membrane.

29. The renal replacement therapy system of claim 28, wherein each of the first, second, and third ion exchange membranes are cation exchange membranes or wherein each of the first, second, and third ion exchange membranes are anion exchange membranes.

30. The renal replacement therapy system of claim 23, wherein the bipolar membrane is a first bipolar membrane, wherein the electrodialysis unit comprises a cell including the first bipolar membrane, a second bipolar membrane, a first ion exchange membrane, and a second ion exchange membrane, and wherein the first ion exchange membrane and the second ion exchange membrane are positioned between the first bipolar membrane and the second bipolar membrane, thereby forming a first compartment between the first bipolar membrane and the first ion exchange membrane, a second compartment between the first ion exchange membrane and the second ion exchange membrane, and a third compartment between the second ion exchange membrane and the second bipolar membrane.

31. The renal replacement therapy system of claim 30, wherein the first ion exchange membrane is a cation exchange membrane and the second ion exchange membrane is an anion exchange membrane.

32. The renal replacement therapy system of claim 23, wherein a power source in the urea decomposition unit provides the electrodes with an electrical charge to activate the electrocatalytic surface of the electrodes.

33. The renal replacement therapy system of claim 23, wherein a power source in the electrodialysis unit provides the electrodes with an electrical charge to split water in the bipolar membrane into $H^+$ and $OH^-$.

34. The renal replacement therapy system of claim 23, wherein the electrodialysis unit separates the dialysis fluid having urea via bipolar membrane electrodialysis.

35. The renal replacement therapy system of claim 23, wherein the dialysis fluid includes one or more substance selected from the group consisting of: a sodium salt, a magnesium salt, a calcium salt, lactate, carbonate, acetate, citrate, and phosphate.

36. The renal replacement therapy system of claim 23, further comprising a tank for the dialysis fluid having urea.

37. The renal replacement therapy system of claim 23, wherein the basic stream includes NaOH.

38. The renal replacement therapy system of claim 23, wherein the acid stream includes HCl.

39. The renal replacement therapy system of claim 23, wherein the electrocatalytic surface for decomposition of urea comprises a transition metal and/or mixtures thereof and/or alloys thereof.

40. The renal replacement therapy system of claim 39, wherein the transition metal is cobalt, copper, iron, nickel, platinum, palladium, iridium, ruthenium, or rhodium.

41. The renal replacement therapy system of claim 39, wherein the anode in the urea decomposition unit comprises nickel, nickel oxide, nickel hydroxide or nickel oxide hydroxide (NiOOH).

42. The renal replacement therapy system of claim 23, wherein the urea decomposition unit includes an alkaline polymeric gel.

43. The renal replacement therapy system of claim 23, wherein a voltage difference applied across the cathode and the anode in the urea decomposition unit is sufficient to produce nitrogen gas, carbon dioxide gas, and water.

* * * * *